United States Patent [19]

Carceller et al.

[11] Patent Number: 5,969,107
[45] Date of Patent: Oct. 19, 1999

[54] ANTI-IDIOTYPIC ANTIBODIES WHICH INDUCE AN IMMUNE RESPONSE AGAINST EPIDERMAL GROWTH FACTOR RECEPTOR

[75] Inventors: Ana Carceller; Elisabet Rosell, both of Barcelona; Alicia Gomez, Premia de Dalt; Jaume Adan, Mataro; Jaume Piulats, Barcelona, all of Spain

[73] Assignee: Merck Patent Gesellschaft mit beschrankter Haftung, Darmstadt, Germany

[21] Appl. No.: 08/653,402

[22] Filed: May 24, 1996

[30] Foreign Application Priority Data

May 26, 1995 [EP] European Pat. Off. ............. 95107967

[51] Int. Cl.$^6$ ..................... C07K 16/00; A61K 39/395
[52] U.S. Cl. ..................... 530/387.2; 530/387.1; 530/387.7; 530/388.1; 530/388.23; 530/388.8; 530/388.85; 530/387.3; 424/130.1; 424/131.1; 424/138.1; 424/141.1; 424/152.1; 424/155.1; 424/172.1; 424/174.1
[58] Field of Search .............................. 530/387.3, 387.1, 530/387.2, 387.7, 388.1, 388.23, 388.8, 388.85; 421/130.1, 131.1, 138.1, 141.1, 152.1, 155.1, 172.1, 174.1

[56] References Cited

U.S. PATENT DOCUMENTS 4,918,164  4/1990  Hellstrom et al. .................. 530/387
5,344,760  9/1994  Harvey et al. .
5,459,061  10/1995  Sato et al. ......................... 435/240.27

FOREIGN PATENT DOCUMENTS 141783    10/1984  European Pat. Off. .
0 176 355  4/1986  European Pat. Off. .
0 586 002  3/1994  European Pat. Off. .
92/15683  9/1992  WIPO .

OTHER PUBLICATIONS

Chanh et al (PNAS, 84;3891–3895), 1987.
Rodeck et al., "Monoclonal Antibody 425 Inhibits Growth Stimulation . . . ", *J. of Cellular Biochemistry*, vol. 44:69–79, 1990.
Kettleborough et al., "Humanization of a mouse monoclonal antibody . . . ", *Protein Engineering*, 4(7):773–783, 1991.
Murthy et al., "Binding of an Antagonistic Monoclonal Antibody to . . . ", *Archives of Biochemistry and Biophysics*, 262(2):549–560, 1987.
Carter et al., "Humanization of an anti–p185$^{HER2}$ antibody for . . . ", *Proc. Natl. Acad. Sci. USA*, vol. 89:4285–4289, 1992.
Rodeck et al., "Tumor Growth Modulation by a Monoclonal Antibody to . . . ", *Cancer Research*, vol. 47:3692–3696, 1987.
Merimsky et al., "Antigens and Antibodies in Malignant Melanoma," *Tumor Biol.*, 15:188–202, 1994 [and Abstract].
Steiner et al., "Distribution of Humanized MAb 425 (EMD 62 000) . . . ," *Cellular and Molecular Biology*, 41(1):179–184, 1995.
Tsujusaki et al., "The Analysis of Internal Image–Bearing . . . ," *J. of Immun.*, 15(2):508–516, Jan. 15, 1993.
Suárez et al., "Anti–idiotype monoclonal antibodies recognizing . . . ," *Immunologia:Monoclonal Antibody Rpts.*, 12:122–123, 1993.
Queen et al CPNAS, 1989, 86: 10029–10033.

*Primary Examiner*—Paula K. Hutzell
*Assistant Examiner*—Susan Ungar
*Attorney, Agent, or Firm*—Millen, White, Zelano & Branigan, P.C.

[57] ABSTRACT

The present invention relates to anti-idiotypic antibodies which induce an immune response against tumors, bearing as antigen the epidermal growth factor receptor (EGFR). The antibodies of the invention may mimic said antigen. As preferred embodiment the antibodies of the invention derive from mAB 425 (ATCC HB 9629) or a humanized or chimeric derivative thereof.

8 Claims, 13 Drawing Sheets

Leader
ATG GAC TCC AGG CTC AAT TTA GTT TTC CTT GTC CTT GTT TTG AAA GGT
Met Asp Ser Arg Leu Asn Leu Val Phe Leu Val Leu Val Leu Lys Gly
           FR1
GTC CAG TGT GAA GTG CAA CTG GTG GAG TCT GGG GGA GGC TTA GTG AAG
Val Gln Cys Glu Val Gln Leu Val Glu Ser Gly Gly Gly Leu Val Lys CCT GGA GGG TCC CTG AAA CTC TCC TGT GCA GCC TCT GGA TTC ACT TTC
Pro Gly Gly Ser Leu Lys Leu Ser Cys Ala Ala Ser Gly Phe Thr Phe CDR1                    FR2
AGT *GAC TAT TAC ATG TAT* TGG TTT CGC CAG CAT CCG GGA AAG AGG CTG
Ser *Asp Tyr Tyr Met Tyr* Trp Phe Arg Gln His Pro Gly Lys Arg Leu CDR2
GAG TGG GTC GCA *ACC ATT AGT GAT GCT GGT ACT TAC ACC TAC TAT CCA*
Glu Trp Val Ala *Thr Ile Ser Asp Ala Gly Thr Tyr Thr Tyr Tyr Pro*

FR3
*GAC AGT CTG AAG GGG* CGA TTC ACC ATC TCC AGA GAC AAT GCC AAG AAC
*Asp Ser Leu Lys Gly* Arg Phe Thr Ile Ser Arg Asp Asn Ala Lys Asn

AAC CTG TAC CTC CAA ATG AGC AGT CTG AAG TCT GAG GAC ACA GCC ATG
Asn Leu Tyr Leu Gln Met Ser Ser Leu Lys Ser Glu Asp Thr Ala Met

CDR3
TAT TTC TGT GCA AGA *GAC GGG GCA GCT CGG ACT TCG TCC CAG GTT TAT*
Tyr Phe Cys Ala Arg *Asp Gly Ala Ala Arg Thr Ser Ser Gln Val Tyr*

FR4
*TAC TAT GGT ATG GAC TAC* TGG GGT CAA GGA ACC TCA GTC ACC GTC TCC
*Tyr Tyr Gly Met Asp Tyr* Trp Gly Gln Gly Thr Ser Val Thr Val Ser

Mouse constant IgG1
TCA GCC AAA ACG ACA CCC CCA TCT GTC TAT CCA TTC CCG GGT TCC
Ser Ala Lys Thr Thr Pro Pro Ser Val Tyr Pro Phe Pro Gly Ser

FIG. 5A

Leader
ATG GGC TTC AAG ATG GAG TCA CAT ATT CAG GTC TTT GTA TTC GTG TTG
Met Gly Phe Lys Met Glu Ser His Ile Gln Val Phe Val Phe Val Leu

FR1
CTC TGG TTG TCT GGT GTT GAT GGA GAC ATT GTG ATG ACC CAG TCT CAA
Leu Trp Leu Ser Gly Val Asp Gly Asp Ile Val Met Thr Gln Ser Gln

CDR1
AAA TTC ATG TCC ACA TCA GTA GGA GAC AGG GTC AGC ATC ACC TGC *AAG*
Lys Phe Met Ser Thr Ser Val Gly Asp Arg Val Ser Ile Thr Cys *Lys*

FR 2
*GCC AGT CAG AAT GTT CGT ACT GCT GTA GCC* TGG TAT CAA CAG AAA CCA
*Ala Ser Gln Asn Val Arg Thr Ala Val Ala* Trp Tyr Gln Gln Lys Pro

CDR2
GGG CAG TCT CCT AAA GCA CTG ATT TAC *TTG GCA TCC AAC CGG CAC ACT*
Gly Gln Ser Pro Lys Ala Leu Ile Tyr *Leu Ala Ser Asn Arg His Thr*

FR 3
GGA GTC CCT GAT CGC TTC ACA GGC AGT GGA TCT GGG ACA GAT TTC ACT
Gly Val Pro Asp Arg Phe Thr Gly Ser Gly Ser Gly Thr Asp Phe Thr

CTC ACC ATT AGC AAT GTG CAA TCT GAA GAC CTG GCA GAT TAT TTC TGT
Leu Thr Ile Ser Asn Val Gln Ser Glu Asp Leu Ala Asp Tyr Phe Cys

CDR3                                    FR4
*CTG CAA CAT TGG AAT TAT CCT CTC ACG* TTC GGC TCG GGG ACA AAG TTG
*Leu Gln His Trp Asn Tyr Pro Leu Thr* Phe Gly Ser Gly Thr Lys Leu

Mouse constant kappa
GAA ATA AAA CGG GCT GAT GCT GCA CCA ACT GTA TCC ATC TTC CCA CCA
Glu Ile Lys Arg Ala Asp Ala Ala Pro Thr Val Ser Ile Phe Pro Pro TCC ACC CGG
Ser Thr Arg

FIG. 5B

Leader
ATG GAC TCC AGG CTC AAT TTA GTT TTC CTT GTC CTT GTT TTA AAA GGT
Met Asp Ser Arg Leu Asn Leu Val Phe Leu Val Leu Val Leu Lys Gly
       FR1
GTC CTG TGT GAC GTG AAG CTC GTG GAG TCT GGG GGA GGC TTA GTG AAG
Val Leu Cys Asp Val Lys Leu Val Glu Ser Gly Gly Gly Leu Val Lys CTT GGA GGG TCC CTG AAA CTC TCC TGT GCA GCC TCT GGA TTC ACT TTC
Leu Gly Gly Ser Leu Lys Leu Ser Cys Ala Ala Ser Gly Phe Thr Phe CDR 1          FR2
AGT *AAC TAT TAC ATG TCT* TGG GTT CGC CAG ACT CCA GAG AAG AGG CTG
Ser *Asn Tyr Tyr Met Ser* Trp Val Arg Gln Thr Pro Glu Lys Arg Leu CDR 2
GAG TTT GTC GCA GCC *ATT AAT AGT AAT GGT GGT AGC ACC TAC TAT CCA*
Glu Phe Val Ala Ala *Ile Asn Ser Asn Gly Gly Ser Thr Tyr Tyr Pro*

FR3
*GAC ACT GTG AAG GGC* CGA TTC ACC ATC TCC AGA GAC AAT GCC AAG AAC
*Asp Thr Val Lys Gly* Arg Phe Thr Ile Ser Arg Asp Asn Ala Lys Asn

ACC CTG TAC CTG CAA ATG AGC AGT CTG AAG TCT GAG GAC ACA GCC TTG
Thr Leu Tyr Leu Gln Met Ser Ser Leu Lys Ser Glu Asp Thr Ala Leu

CDR 3
TAT TAC TGT GCA AGA *CAT CGG GGG AGG GAC AGC TCG GGC TAC GTA GGG*
Tyr Tyr Cys Ala Arg *His Arg Gly Arg Asp Ser Ser Gly Tyr Val Gly*
                         FR4
*TAT TCT ATA GAC TAC* TGG GGT CAA GGA ACC TCA GTC ACC GTC TCC TCA
*Tyr Ala Ile Asp Tyr* Trp Gly Gln Gly Thr Ser Val Thr Val Ser Ser mouse constant IgG1
GCC AAA ACG ACA CCC CCA TCT GTC TAT CCA TTC CCG GGT TCC
Ala Lys Thr Thr Pro Pro Ser Val Tyr Pro Phe Pro Gly Ser

FIG. 5C

Leader
ATG GAG TCA GAC ACA CTC CTG CTA TGG GTA CTG CTG CTC TGG GTT CCA
Met Glu Ser Asp Thr Leu Leu Leu Trp Val Leu Leu Leu Trp Val Pro
                FR1
GGT TCC ACT GGT GAC ATT GTG CTG ACA CAG TCT CCT GCT TCC TTA GCT
Gly Ser Thr Gly Asp Ile Val Leu Thr Gln Ser Pro Ala Ser Leu Ala
                                      CDR1
GTA TCT CTG GGG CAG AGG GCC ACC ATC TCA TAC *AGG GCC AGC AAA AGT*
Val Ser Leu Gly Gln Arg Ala Thr Ile Ser Tyr *Arg Ala Ser Lys Ser*

FR2
*GTC AGT ACA TCT GGC TAT AGT TAT ATG CAC* TGG AAC CAA CAG AAA CCA
*Val Ser Thr Ser Gly Tyr Ser Tyr Met His* Trp Asn Gln Gln Lys Pro

CDR2
GGA CAG CCA CCC AGA CTC CTC ATC TAT *CTT GTA TCC AAC CTA GAA TCT*
Gly Gln Pro Pro Arg Leu Leu Ile Tyr *Leu Val Ser Asn Leu Glu Ser*

FR3
GGG GTC CCT GCC AGG TTC AGT GGC AGT GGG TCT GGG ACA GAT TTC ACC
Gly Val Pro Ala Arg Phe Ser Gly Ser Gly Ser Gly Thr Asp Phe Thr

CTC AAC ATC CAT CCT GTG GAG GAG GAG GAT GCC TCA ACC TAT TAC TGT
Leu Asn Ile His Pro Val Glu Glu Glu Asp Ala Ser Thr Tyr Tyr Cys

CDR3                                FR4
*CAG CAC ATT AGG GAG GTC TAC ACG* TTC GGA GGG GGG ACC AAG CTG GAA
*Gln His Ile Arg Glu Val Tyr Thr* Phe Gly Gly Gly Thr Lys Leu Glu

Mouse constant kappa
ATA AAA CGG GCT GAT GCT GCA CCA ACT GTA TCC ATC TTC CCA CCA TCC
Ile Lys Arg Ala Asp Ala Ala Pro Thr Val Ser Ile Phe Pro Pro Ser ACC CGG
Thr Arg

FIG. 5D

Leader
ATG GAC TTT GGG CTC AGC TTG ATT TTC CTT GTC CTT GTT TTT AAA GGT
Met Asp Phe Gly Leu Ser Leu Ile Phe Leu Val Leu Val Phe Lys Gly FR1
GTC CTG TGT GAC GTG AAG CTC GTG GAG TCT GGG GGA GGC TTA GTG AAG
Val Leu Cys Asp Val Lys Leu Val Glu Ser Gly Gly Gly Leu Val Lys CTT GGA GGG TCC CTG AAA CTA TCC TGT GCA GCC TCT GGA TTC ACT TTC
Leu Gly Gly Ser Leu Lys Leu Ser Cys Ala Ala Ser Gly Phe Thr Phe CDR1                  FR2
AGT *AAC TAT TAC ATG TCT* TGG GTT CGC CAG ACT CCA GAG AAG AGG CTG
Ser *Asn Tyr Tyr Met Ser* Trp Val Arg Gln Thr Pro Glu Lys Arg Leu CDR2
GAG TTT GTC GCA GCC *ATT AAT AGT AAT GGT GGT AGC ACC TAC TAT CCA*
Glu Phe Val Ala Ala *Ile Asn Ser Asn Gly Gly Ser Thr Tyr Tyr Pro*

FR3
*GAC ACT GTG AAG GGC* CGA TTC ACC ATC TCC AGA GAC AAT GCC AAG AAC
*Asp Thr Val Lys Gly* Arg Phe Thr Ile Ser Arg Asp Asn Ala Lys Asn

ACC CTG TAC CTG CAA ATG AGC AGT CTG AAG TCT GAG GAC ACA GCC TTG
Thr Leu Tyr Leu Gln Met Ser Ser Leu Lys Ser Glu Asp Thr Ala Leu

CDR3
TAT TAC TGT GCA AGA *CAT CGG GGG AGG GAC AGC TCG GGC TAC GTA GGG*
Tyr Tyr Cys Ala Arg *His Arg Gly Arg Asp Ser Ser Gly Tyr Val Gly*

FR4
*TAT GCT ATA GAC TAC* TGG GGT CAA GGA ACC TCA GTC ACC GTC TCC TCA
*Tyr Ala Ile Asp Tyr* Trp Gly Gln Gly Thr Ser Val Thr Val Ser Ser mouse constant IgG1
GCC AAA ACG ACA CCC CCA TCT GTC TAT CCA TTC CCG GGT TCC
Ala Lys Thr Thr Pro Pro Ser Val Tyr Pro Phe Pro Gly Ser

FIG. 5E

Leader
ATG GTG TCC ACA GCT CAG TTC CTT GTA TTT TTG CTT TTC TGG ATT CCA
Met Val Ser Thr Ala Gln Phe Leu Val Phe Leu Leu Phe Trp Ile Pro FR1
GCC TCC AGA GGT GAC ATC TTG CTG ACT CAG TCT CCA GCC ATC CTG TCT
Ala Ser Arg Gly Asp Ile Leu Leu Thr Gln Ser Pro Ala Ile Leu Ser CDR1
GTG AGT CCA GGA GAA AGA GTC AGT TTC TCC TGC *AGG GCC AGT CAG AGC*
Val Ser Pro Gly Glu Arg Val Ser Phe Ser Cys *Arg Ala Ser Gln Ser*

FR2
*ATT GGC ACA AGC ATA CAC* TGG TAT CAA CAA AGA ACA AAT GGT TCT CCA
*Ile Gly Thr Ser Ile His* Trp Tyr Gln Gln Arg Thr Asn Gly Ser Pro

CDR2                        FR3
AGG CTT CTC ATA AGT *ATA CTT CTG AGT CTA TCT CTG* GGA GTC CCT TCC
Arg Leu Leu Ile Ser *Ile Leu Leu Ser Leu Ser Leu* Gly Val Pro Ser

AGG TTT AGT GGC AGT GGA TCA GGG ACA GAT TTT ACT CTT AGC ATC AAC
Arg Phe Ser Gly Ser Gly Ser Gly Thr Asp Phe Thr Leu Ser Ile Asn

CDR3
AGT GTG GAG TCT GAA GAT ATT GCA GAT TAT TAC TGT *CAA CAA AGT AAT*
Ser Val Glu Ser Glu Asp Ile Ala Asp Tyr Tyr Cys *Gln Gln Ser Asn*

FR4
*AGC TGG CCA TAC ACG* TTC GGA GGG GGG ACC AAG TTG GAA ATA AAA CGG
*Ser Trp Pro Tyr Thr* Phe Gly Gly Gly Thr Lys Leu Glu Ile Lys Arg

Mouse constant kappa
GCT GAT GCT GCA CCA ACT GTA TCC ATC TTC CCA CCA TCC ACC CGG
Ala Asp Ala Ala Pro Thr Val Ser Ile Phe Pro Pro Ser Thr Arg

FIG. 5F

ANTI-IDIOTYPIC ANTIBODIES WHICH INDUCE AN IMMUNE RESPONSE AGAINST EPIDERMAL GROWTH FACTOR RECEPTOR

FIELD OF THE INVENTION

The present invention is directed to anti-idiotypic antibodies which induce an immune response against tumors which bear as antigen the epidermal growth factor receptor (EGFR). This invention relates to anti-idiotypic antibodies which have the internal image of an antigen and which mimic an external domain of an EGFR. As preferred embodiments of the invention, said antibodies derive from the murine mAb 425 or from its humanized and chimeric versions. The antibodies of the invention can be used for tumor immunotherapy and immunoprophylaxis.

DETAILED DESCRIPTION OF THE INVENTION

Figure 1:
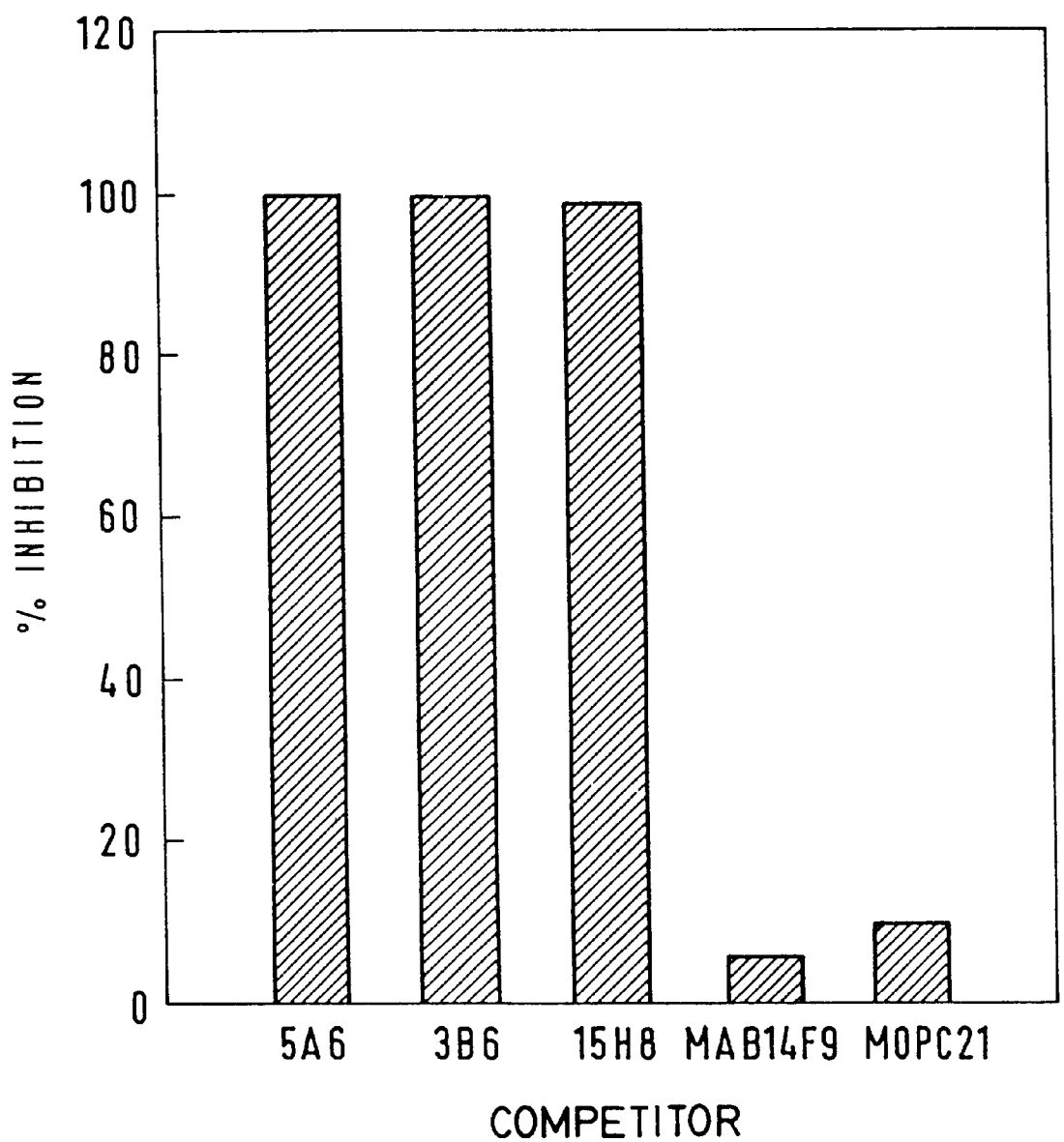

The specification relates to several abbreviations and technical terms which are defined as follows:

"FRs" (framework regions) mean the four subregions of the light or heavy chain variable regions that support the three CDRs.

"CDRs" (complementarity determining regions) mean the three subregions of the light or heavy chain variable regions which have hypervariable sequences and form loop structures that are primarily responsible for making direct contact with antigen.

"EGF" and "EGFR" mean the epidermal growth factor and its receptor.

"PCR" means the polymerase chain reaction.

"scFv" means single-chain Fv which is an antibody fragment.

"$V_L$" means light chain variable region.

"$V_K$" means kappa light chain variable region.

"$V_H$" means heavy chain variable region.

"Chimeric" or partially humanized antibodies mean antibodies comprising constant regions deriving from human sources and variable regions (CDRs included) deriving from non-human sources, e.g. from the mouse.

"Humanized" or fully humanized antibodies mean antibodies comprising constant regions and FRs deriving from human sources whereas the CDRs derive from non-human sources.

"Ab1" means the first or parent antibody which induces a cascade of succession antibodies by immunisation.

"Ab2" means the typical anti-idiotypic antibody (="anti-id") which is directed to the idiotypes of the Ab1.

"Ab3" means an anti-idiotypic antibody which is directed against the idiotypes of the Ab2, and thus, is comparable with Ab 1.

PBS means phosphate buffered saline
FCS means fetal calf serum
HBSS means Hanks balanced salt solution
FITC means fluoresceineisothiocyanate
MTC means mixed cell culture
KLH means Keyhole Limpet Hemocyanine
CFA means complete Freund's adjuvants
HRPO means human recombinant peroxidase Anti-idiotypic antibodies (anti-idotypes or "anti-ids") are antibodies directed against epitopes (called idiotypes) located in the antigen binding region or variable region of another antibody molecule. The interactions between idiotypes (Ab1) and anti-idiotypes (Ab2) play an important role in the maintenance of immune homeostasis. A network of idiotypes and anti-idiotypes has been invoked to explain immunregulation (Jerne, F. G., 1974, Ann.Immunol.125C: 373). The "internal image" anti-idiotypic antibodies mimic the three-dimensional structure of the antigen recognized by the Ab1. The administration of Ab2 can induce the production of Ab3 antibodies against the original antigen. Idiotype vaccines have been applied successfully on several transmissible diseases and in the treatment of cancer (for example:

Uytdehaag, F. G., and C. M. H. Osterhaus, 1986, J.Immunol.134:1225; Kennedy, R. C. et al. 1986, Science 232:220; Hiernaux J. R, 1988; 56:1407; Stein, K. E., and T. Soderstrom,1984, J.Exp.Med. 160:1001). In tumor immunology, the idiotypic vaccination has been used to modulate tumor growth in experimental in vivo and in vitro systems (Smorodinsky, N. I. et al, 1988; Eur. J.Immunol. 18:1713. Viale,G., et al., 1987, J.Immunol. 139:4250). Herlyn et al (1987, Proc.Natl. Acad Sci. USA. 76:1438) have reported promising results in a clinical trial on patients with advanced colorectal carcinoma, arrest of metastases and partial clinical remissions were observed in patients treated only with anti-ids. Anti-idiotypic antibodies and its use for tumor therapy are also known from U.S. Pat. No. 4,918,164 and EP 0141 783, for example.

Epidermal growth factor (EGF) is a polypeptide hormone which is mitogenic for epidermal and epithelial cells. When EGF interacts with sensitive cells, it binds to membrane receptors (EGFR). The EGFR is a transmembrane glycoprotein of about 170 kD and is a gene product of the c-erb-B proto-oncogene.

MAb 425 is a murine monoclonal antibody. It is an anti-idiotypic antibody raised against the well known human A431 carcinoma cell line (ATCC CRL 1555), binds to a polypeptide epitope of the external domain of the human EGFR, inhibits the binding of EGF, inhibits growth of A431, and/or shows EGF-like agonist activity on A431 cells, MAb 425 (ATCC HB 9629) was found to mediate tumor cytotoxicity in in vitro and to suppress tumor cell growth of epidermoid and colorectal carcinoma-derived cell lines in vitro, e.g., A431, (Rodeck et al., Cancer Res. 1987. 47:3692). See also, Rodeck et al., J. Cell. Biochem., 1990. 44:69. An idiotypic antibody according to the present invention can possess one or more of such properties, preferably the idiotypic antibody is a murine monoclonal antibody which binds to a polypeptide epitope of the external domain of human epidermal growth factor receptor and which inhibits binding of EGF and the growth of A431 cells. Humanized and chimeric versions of MAb 425 have been disclosed in WO 92/15683. The binding of the EGF to the receptor activates several biochemical processes leading to DNA replication and cell division (Carpenter, G., 1987, Annu. Rev. Biochem. 56:881). The EGFR system has been recently implicated in oncogenic transformation of cells (DiFiore, P. P. et al.,. 1987, Cell. 51:1063.10). An autocrine stimulated cell proliferation has been proposed for several tumors which express the EGFR and secrete EGF or TGFα (Ennis, B. W. et al., 1989, Mol. Endo. 3:1830), higher expression of EGFR in cell surface has been detected in tumors of diverse tissue origin: breast, bladder, carcinomas, melanomas and non-neuronal brain tumors (Neal, D. E. et al., 1985; Lancet 1:366; Libermann, T. A. et al., 1984, Cancer Res. 44:753; Herlyn, M. et al., 1982, J. Clin. Immunol. 2:135). EGFR is a therapeutical target because it is directly implicated in cellular proliferation of several tumors. Its overexpression has shown to be of bad prognostic value, correlating with an augmented invasive potential (Sainsbury, J. R., et al., 1985, Lancet 1:364).

The passive or active immunization against EGFR in cancer patients leads to circulating specific antibodies which act as antagonists of EGF and TGFα, blocking their access to the receptor and inhibiting tumor growth. EGFR is a good candidate for an Idiotype vaccine since it can be purified from tumor cells but is not available in amounts sufficient for therapeutic purposes.

Anti-idiotypic antibodies, in general, and their structural comparison with their antigens, and internal images, were investigated and discussed by several groups (e.g., Tsjisaki, M. et al., 1993, *J. Immunol.* 150:508; Raychaudhuri, S. et al., 1990, *J. Immunol.* 145:760; Bruck, C. et al., 1986, *Proc. Natl. Acad. Sci. USA* 83:6578).

The present invention provides for the first time new anti-idiotypic antibodies (anti-ids) which induce an immune response against the epidermal growth factor receptor. Especially, the invention provides at least two such anti-ids (designated as 5A6 and 3B6) which mimic an antigen site on the surface of the human epidermal growth factor receptor. Thus, the antibodies according to the invention, especially those that can mimic the EGFR can be used to induce and to increase the immune response against all kinds of human tumors which express the epidermal growth factor receptor on their surface, melanomas, gliomas and carcinomas included. The said antibodies can be used, e.g., for diagnostic and immunological applications, e.g., locating and assessing tumors and other tissues and cells in vitro or in vivo, detecting EGFR in biological samples, standardizing EGFR in biological samples, purification methods, detection methods.

Thus, it is an objection of the invention to provide a new antibody which is a monoclonal anti-idiotypic (Ab2) antibody inducing an immune response against epidermal growth factor receptor (GFR).

In detail, the invention relates to a monoclonal anti-idiotypic antibody mimicking the internal image of EGFR antigen recognized by a corresponding murine, humanized or chimeric, monoclonal idiotypic (Ab1) antibody. This Ab1 antibody can be a non-human, especially a murine, a humanized or a chimeric monoclonal antibody as defined above. The invention relates also to anti-idiotypic antibodies which can be recognized by Ab1 anti-EGFR antibodies.

The invention relates, furthermore, to monoclonal anti-idiotypic anti-EGFR antibodies which can be obtained from the corresponding Ab1 anti-EGFR antibody, for example, by immunization.

Therefore, it is an object of the present invention to provide a monoclonal anti-idiotypic antibody which is obtainable by immunization of an animal with a corresponding murine, humanized or chimeric, idiotypic (Ab1) antibody. The anti-idiotypic antibodies of the invention are preferably obtained by immuniazation with the monoclonal anti-EGFR antibody 425 or humanized chimeric versions thereof of an antibody having its characteristics (e.g., Rodeck et al., *Cancer Res.* 1987). MAb 425 is produced by the known cell line deposited under ATCC HB 9629 which was deposited with the ATCC, 12301 Parklawn Dr., Rockville, Md., USA, in accordance with the Budapest Treaty, and is now publicly available.

Thus, it is an object of the invention to provide a monoclonal antibody characterized in that the idiotypic (Ab1) antibody is mAb 425 (ATCC HB 9629) or an antibody having its characteristics (e.g., Rodeck et al., *Canc. Res.* 1987) or derives from it by humanisation or chimerisation according to known methods, for example, as described in WO 92/15683.

The invention relates also to specific anti-idiotypic antibodies which have well defined amino acid sequences in the hypervariable (CDRs) and variable (FRs) regions of the antibodies and which are indicated in FIGS. 5A–F (SEQ ID NO: 1 to SEQ ID NO: 12).

Therefore, it is another object of the invention to provide an anti-idiotypic monoclonal antibody wherein the CDR regions and the FR regions of said antibody comprise the amino acid sequences of FIGS. 5A–F (SEQ ID NO: 1 to SEQ ID NO: 12). Moreover, it is an object of the invention to provide, as preferred embodiment, an anti-idiotypic antibody comprising an amino acid or a nucleotide sequence of FIGS. 5A–F (SEQ ID NO:1 to SEQ ID NO: 12).

Upon further study of the specification and appended claims, further objects and advantages of this invention will become apparent to those skilled in the art. According to the invention, the disclosed sequences comprise also variations and changes which derive from the exactly specified sequences of FIG. 5 by spontaneous or induced chemically or physically caused mutations, insertions, deletions and replacements of single amino acid or nucleotide residues, provided that the biological activity and properties of the final antibodies have not been essentially altered.

The term anti-idiotypic antibody also includes parts or fragments of such an antibody, for example, single chain Fv molecules of F(ab)'$_2$ and Fab' molecules which are well known in the art (Skerra and Pluckthun, *Science* 1988. 240:1038; Better et al., *Science* 1988. 240:1041) Single chain Fvs (wherein the $V_L$ and the $V_H$ chain are linked together) have been also described (e.g.: Bird et al., *Science* 1988. 242:423; Huston et al., *Proc. Natl. Acad. Sci. USA* 1988. 85:5879). The invention relates, moreover, to a process for the preparation of an anti-idiotypic antibody as defined in the specification and in the claims, characterized in that an animal is immunized with a corresponding idiotypic (Ab1) antibody, which binds to the antigen directly by its CDR regions, the synthesized anti-idiotypic (Ab2) antibody, which binds to the idiotypes of the Ab1 antibody, is separated and purified by convenient methods.

Futhermore, it is an object of the invention to provide a pharmaceutical composition comprising an anti-idiotypic monoclonal antibody as defined in the specification and, optionally, a pharmaceutically acceptable carrier. Finally, the invention relates to the use of said anti-idiotypic antibody for the manufacture of a drug directed against tumors. By the term "isolated," it is meant that the compound, e.g., an antibody, is in a form that occurs in nature, e.g., more concentrated, free of particular components such as blood cells, serum, etc. The present invention describes the obtention of three monoclonal anti-idiotypic antibodies (5A6, 3B6 and 15H8) that recognize idiotypes overlapping with the antigen-binding site (paratope) of mAb 425. The serologic and immunologic studies have shown that 5A6 and 3B6 carry the internal image of the epitope recognized by mAb 425 inducing a humoral response in syngeneic (Balb/c mice) and allogeneic (B6D2F1 mice) system. True internal image Anti-Ids would act as antigen surrogates in animals of different species, however these Anti-Ids have been ineffective to generate Ab1-like response in rabbits and rats.

The cloning and sequencing of their V regions has shown the existence of amino acid homologies between CDRs of both light and heavy chains and some EGFR residues located in the ligand binding domain, indicating antigen mimicry. The study of antigenicity of homologous regions indicates an explanation for the lack of biological effect in a heterogeneic system.

BRIEF DESCRIPTION OF THE FIGURES AND TABLES

FIG. 1: inhibition binding of 425 to sEGFR by 5A6, 3B6, 15H8 or unrelated mAbs. Percentage of inhibition is calculated as described in material and methods using OD values from ELISA.

Figures 1, 3A:
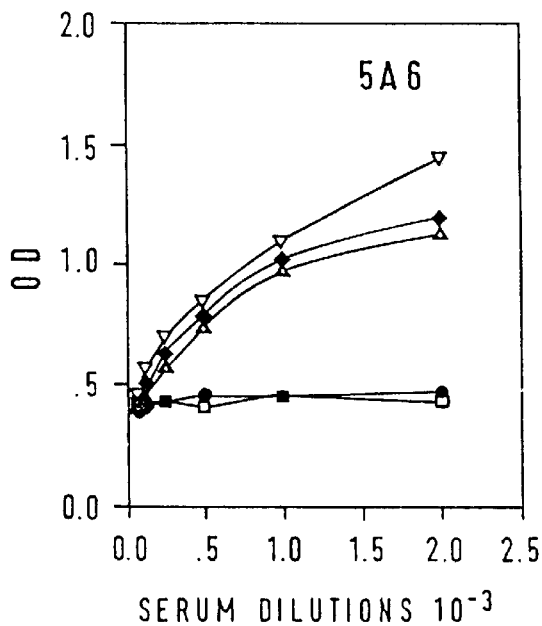
Figures 2, 3A:
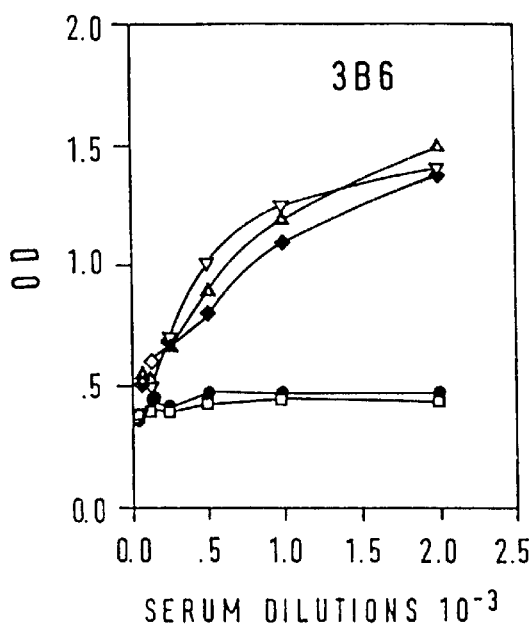

FIG. 2: inhibition binding curves of murine (2A) and humanized version (2B) of 425 to EGFR expressing. A431

Cells by 5A6(●), 3B6 (○), 15H8 (▽) and murine IgG1 (Sigma) (▼). Results are expressed as OD mean of duplicate samples. x-ordinate: competitor (μg/ml), y-ordinate: OD.

Figures 3, 3A:
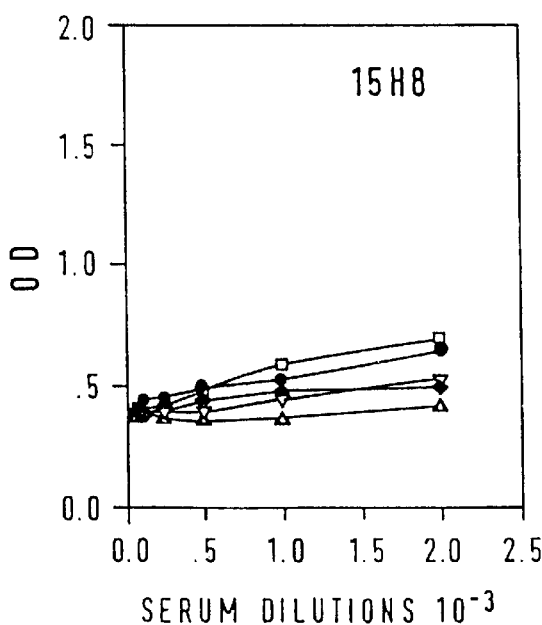

FIG. 3: Competitive ELISA for Ab3–Ab2 binding. Serial dilutions of rat Ab3 sera were tested for binding to solid-phase coated Ab2 or unrelated mAb15, previously incubated with 5A6 (●), 3B6(■) and 15H8(▲). mAb15(▽) and Normal Mouse sera (♦) were used as controls. 3A–D A: rat Ab3 sera anti-5A6; 3E–H: rat Ab3 sera anti-3B6; 3I–L: rat Ab3 sera anti-15H8; 3M–P: rat control sera anti-mAb15; y-ordinate: OD, x-ordinate: serum dilutions×10$^{-3}$.

Figures 3, 3A, 4:
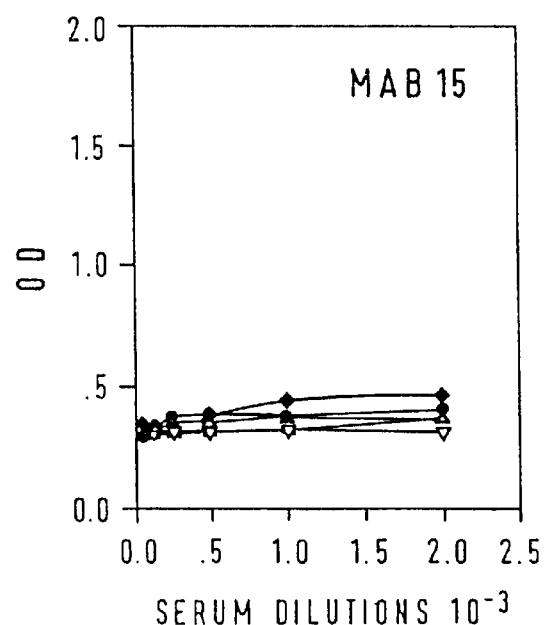
Figures 1, 3B:
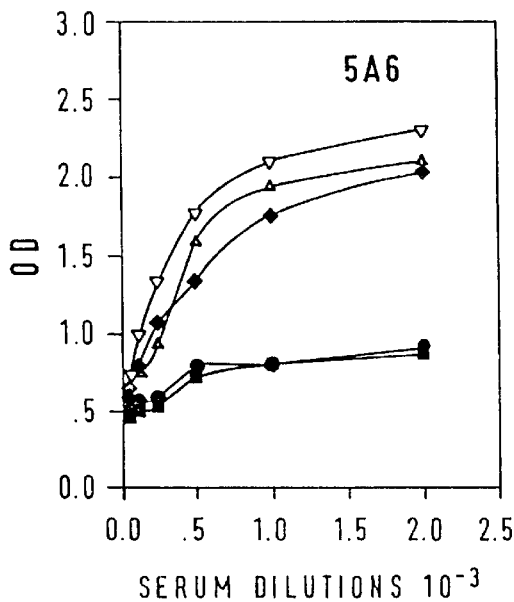
Figures 2, 3B:
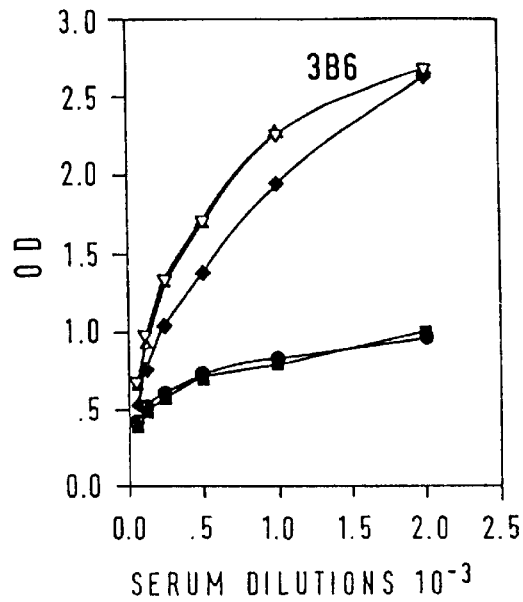
Figures 3, 3B:
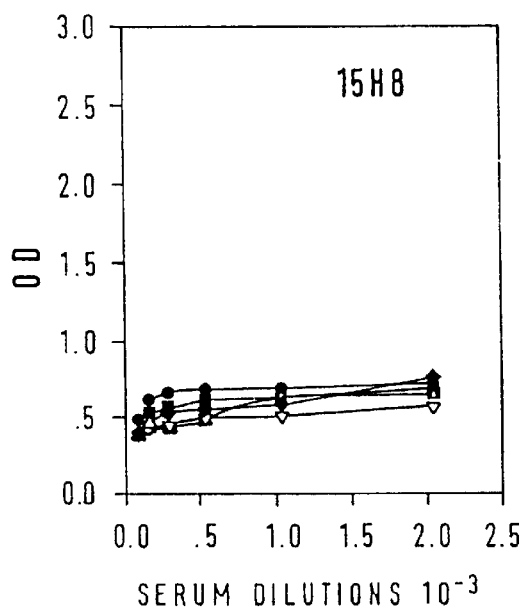
Figures 3, 3B, 4:
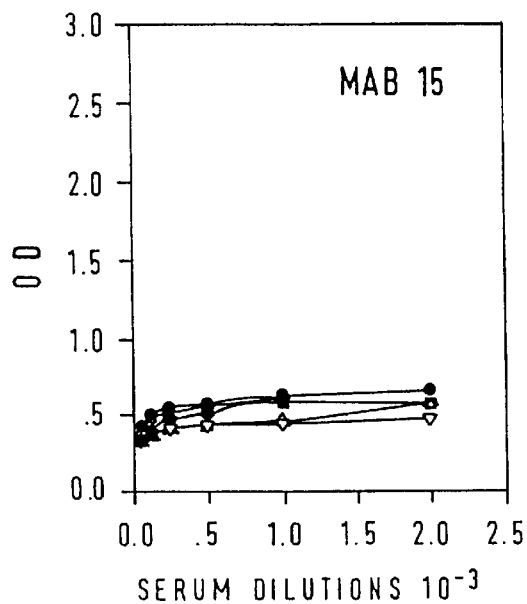
Figures 1, 3C:
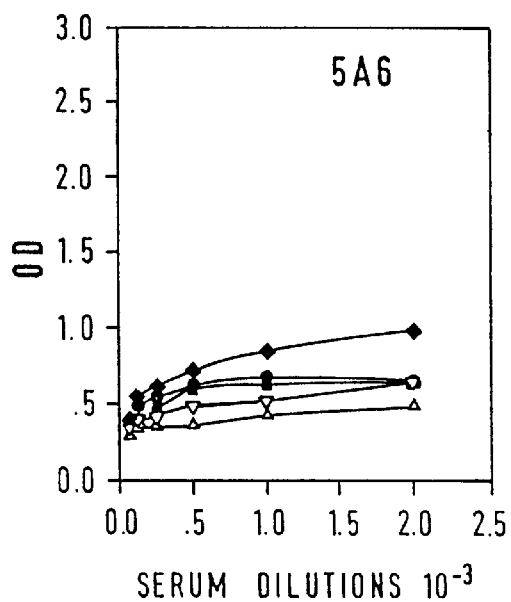
Figures 2, 3C:
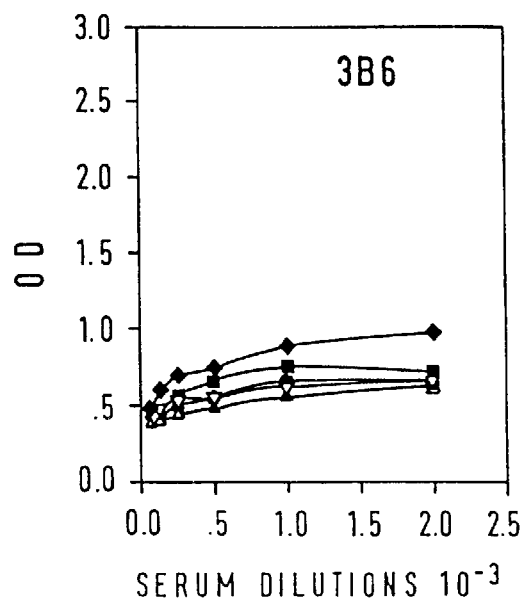
Figures 3, 3C:
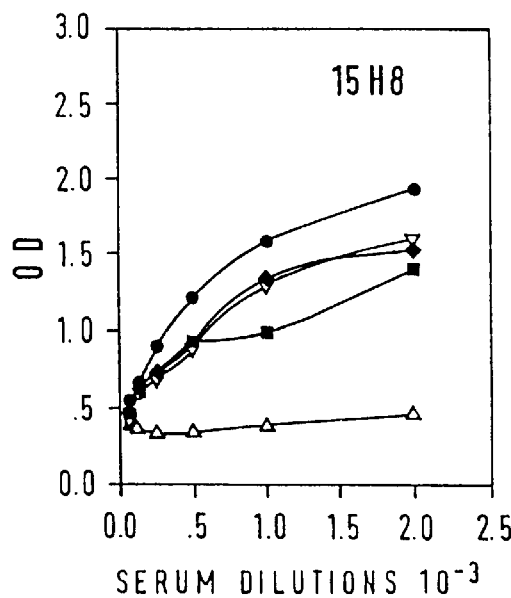
Figures 3, 3C, 4:
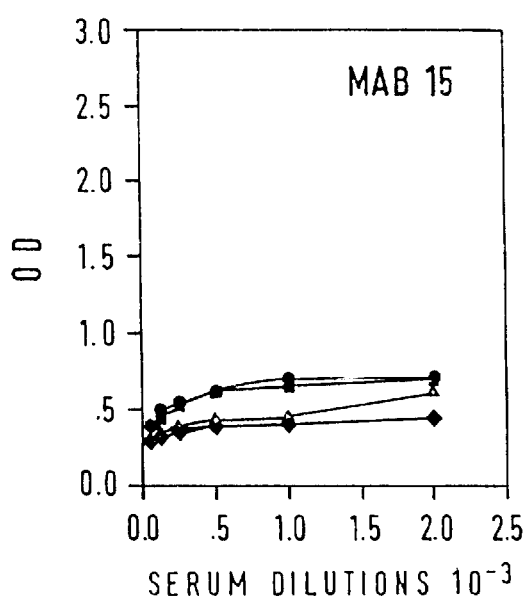
Figures 1, 3D:
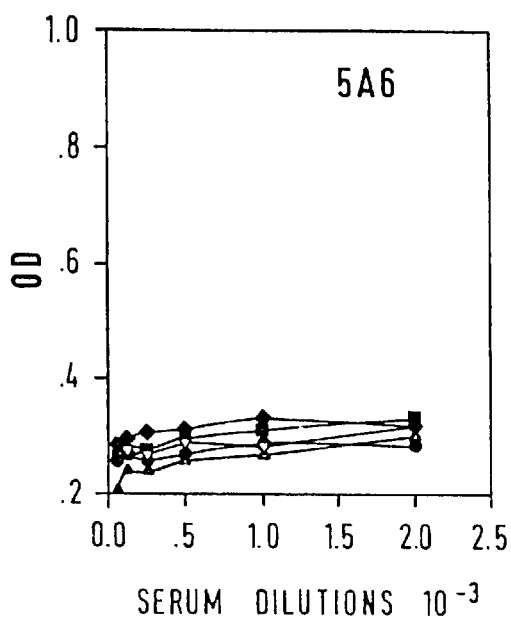
Figures 2, 3D:
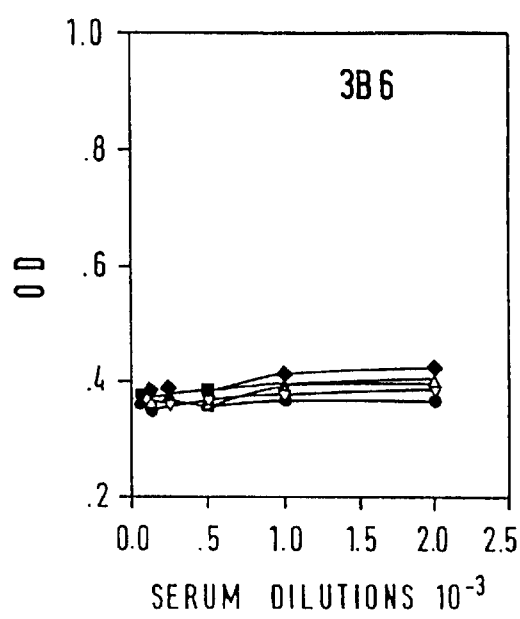
Figures 3, 3D:
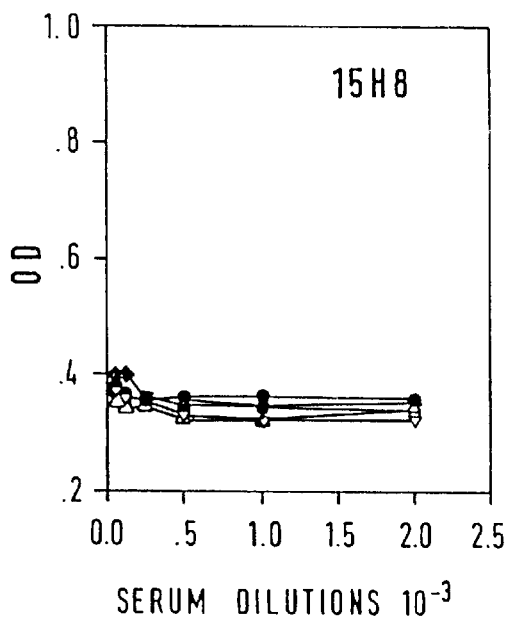
Figures 3, 3D, 4:
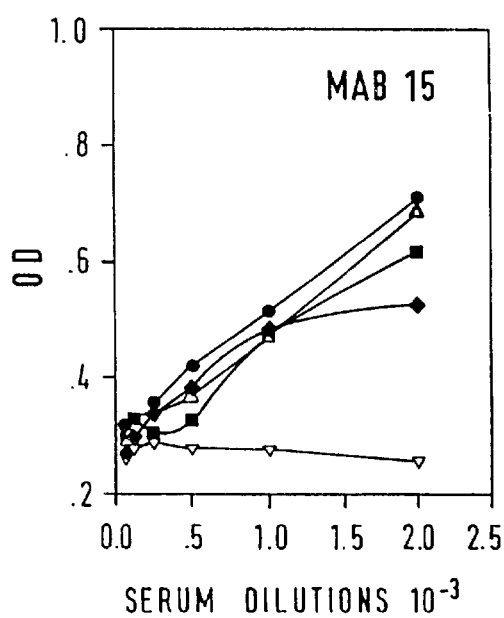
Figure 4:
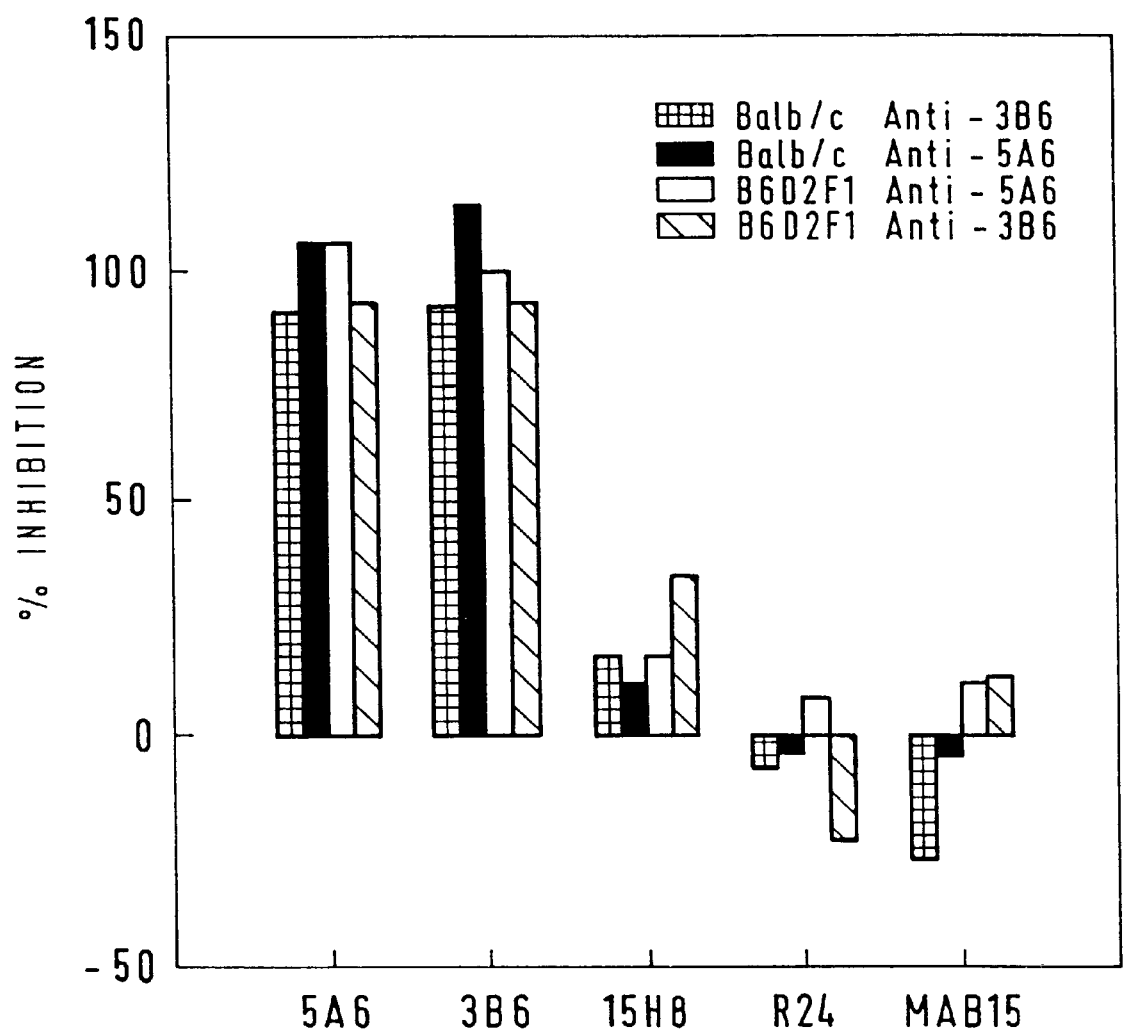

FIG. 4: Solid phase ELISA: Inhibition binding of Balb/c and B6D2F1 Ab3 from 5A6 and 3B6 immunized mice to purified EGFR by Anti-Ids.

FIG. 5: Complete sequence of variable region (including leader sequence) of heavy and light chain of 15H8, 5A6 and 3B6 mouse monoclonal antibodies. The nucleotide and amino acid sequences are shown. The leader sequence if annotated in bold, CDR sequences are in italic and the sequence of the primers used for the amplification of the variable regions are underlined. The heavy chain of 15H8, 5A6 and 3B6 have the characteristic structure of group III D. The light chain of 15H8 and 5A6 have the characteristic structure of kappa group V, and 3B6 has the structure of kappa group III, both according to Kabat classification.

5A: 15H8 heavy chain (having a nucleotide sequence set forth in SEQ ID NO: 1 and having an amino acid sequence set forth in SEQ ID NO:2)

5B: 15H8 light chain (having a nucleotide sequence set forth in SEQ ID NO:3 and having an amino acid sequence set forth in SEQ ID NO:4)

5C: 3B6 heavy chain (having a nucleotide sequence set forth in SEQ ID NO:9 and having an amino acid sequence set forth in SEQ ID NO: 10)

5D: 3B6 light chain (having a nucleotide sequence set forth in SEQ ID NO: 11 and having an amino acid sequence set forth in SEQ ID NO: 12)

5E: 5A6 heavy chain (having a nucleotide sequence set forth in SEQ ID NO:5 and having an amino acid sequence set forth in SEQ ID NO: 6)

5F: 5A6 light chain (having a nucleotide sequence set forth in SEQ ID NO:7 and having an amino acid sequence set forth in SEQ ID NO:8)

Table I. Affinity constants of 5A6, 3B6 and 15H8 for 425. Dissociation constants have been calculated by scatchard plots of binding of Ab2 to 425 from OD values obtained by ELISA performed as described in material and methods.

Table II. Ab1–Ab2 inhibition binding by Ab3 and detection of cross reacting idiotypes on Ab2. Twofold dilutions of Ab3 sera from mice (A), rabbits (B) and rats (C) immunized by Anti-Ids or unrelated mAbs were tested for binding inhibition of their immunizing Ab2, the other Anti-Ids and murine isotype and allotype matched mAbs. Serum titres showing 100% inhibition are given.

Table III. Anti-EGFR response in Balb/c mice determined by indirect immunofluorescence against EGFR positive (A431) or negative (C33A) unfixed cells, by ELISA against whole cells or purified external domain.
a) Detection with FITC rabbit Anti-murine IgM+IgG.
b) Detection with FITC rabbit Anti-murine IgG.
c) Positive anmials/immunized animals.

DETAILED DESCRIPTION
Biological Materials and General Methods

Microorganisms, cell lines, plasmids, phagemids, promoters, resistance markers, replication origins or other fragments of vectors which are mentioned in this application are commercially or otherwise generally available. Provided that no other information in the application is given, they are used only as examples and are not essential according to the invention and can be replaced by other suitable tools and biological materials, respectively.

The techniques which are essential according to the invention are described in detail in the specification. Other techniques which are not described in detail correspond to known standard methods which are well known to a person skilled in the art, or are described more in detail in the cited references and patent applications and in the standard literature (e.g. Harlow,E., and D.Lane. 1988. *Antibodies, a laboratory manual.* Cold Spring Harbor Laboratory, N.Y.)

Balb/c mice (IFFA CREDO), B6D2F1 hybrid strain from C57BL/6J and DBA/2J mice (IFFA CREDO), Wistar Rats (Interfauna Ibérica) and New Zealand White Rabbits (Biocentre) were used for in vivo assays.

A43 1 is an epidermoid carcinoma (ATCC CRL1555) expressing EGFR C33A (ATCC HTB31), a cervical carcinoma, is receptor negative. HL1-Friendly Myeloma-653 (Ventrex, Bioventures group) was used as fusion partner for hybridoma obtention. All lines were cultured in RPMI 1640 Medium supplemented with 10% Fetal Calf Serum and 2mM glutamine. Anti-EGFR mAb 425 (Ab1) was generated according to Rodeck et al. Several murine mAbs of unrelated specificities were used as controls in the different assays: mAb15 (IgG1,k), anti-gp85/45 of small cell lung carcinomas; R24, (IgG3,k), anti-GD3; 14F9 (IgG3,k), anti-GD3 and Me361 (IG2a), anti-GD2 have been previously described (Kanma, H. et al., 1989, *Cancer Res.* 49(8): 5118; Dippold, W. G. et al., 1980, *Proc. Natl. Acad Sci. USA.* 77:6114; Massó. et al.,1991, *Immunologia* 10:36; Thurin, J. et al., 1987, *Cancer Res.* 47:1229).

F111 (IgG1,k) was obtained by PEG-induced fusion between splenocytes from RNase immunized Balb/c mice and Friendly-Myeloma as described below.
Anti425 Idiotype mAb obtention.

Murine hybridomas have been generated using splenocytes from Balb/c mice immunized with mAb 425 and fused with 653-Friendly Myeloma cells. Supernatants were tested by sandwich ELISA against mAb 425. 5A6, 3B6 and 15H8 hybridomas were obtained from two fusions that gave 2.8% and 10.5% specific efficiency respectively described by Carceller (example 1), 1988; *Sangre* 33(3):220. After cloning three times by the limiting dilution method, they were found to be IgG1,k.

Crude supernatants or protein A purified samples were used for Ab2 characterization. The Anti-Id nature was confirmed by their specific binding to mAb 425, when tested against a panel of non-related mAbs with different antigenic specificities. (F111, 361, 15 and 14F9).

To define the localization of 425 idiotopes recognized by anti-Ids, they were tested for 425-EGFR inhibition binding by ELISA against sEGFR. All them completely inhibited mAb 425 reactivity (FIG. 1) with sEGFR indicating that they recognize idiotopes within the antigen binding site.

Figure 2A:
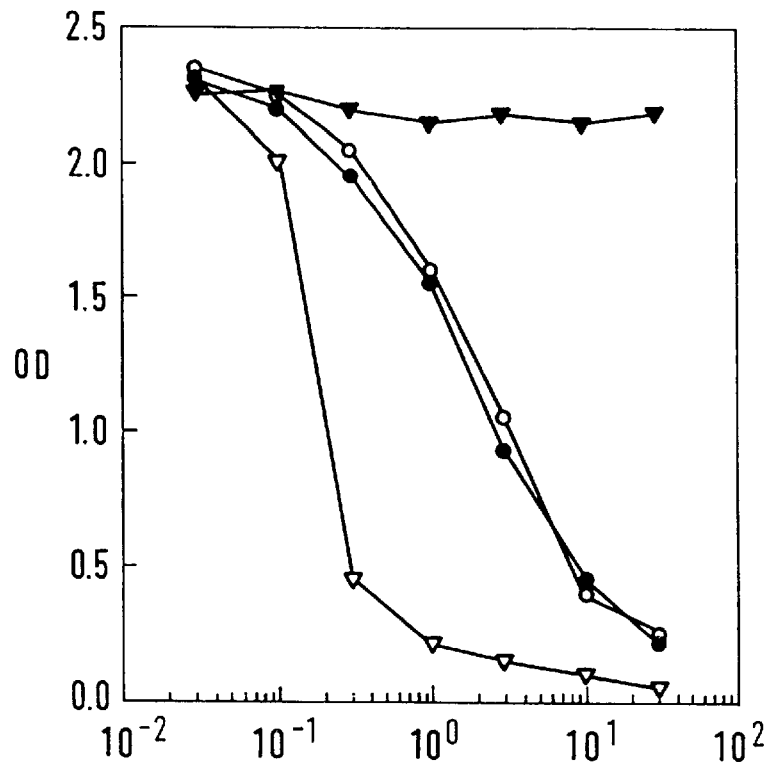
Figure 2B:
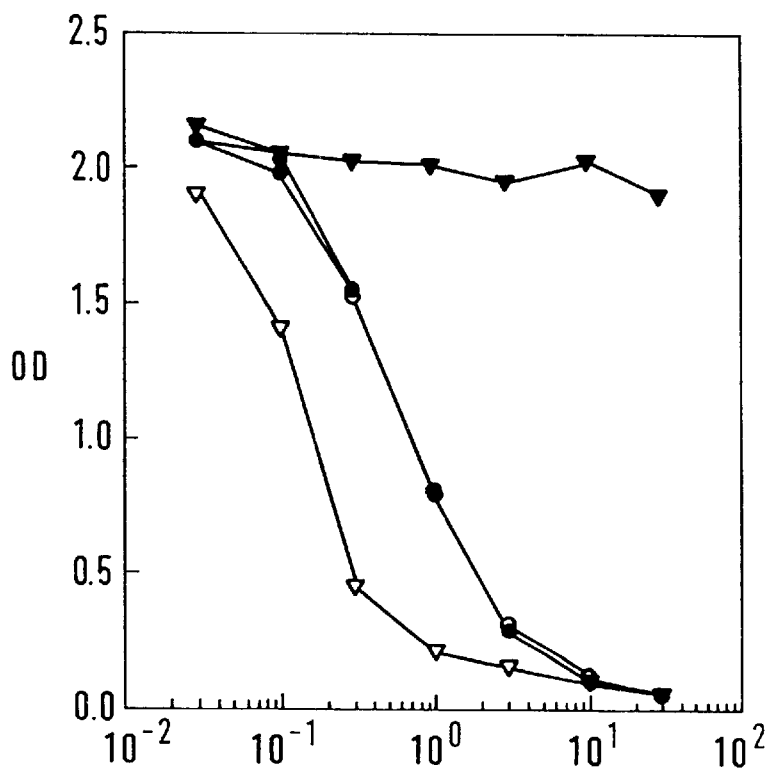

To define 5A6, 3B6 and 15H8 Anti-Ids as Ab2 we determined whether the idiotopes recognized on mAb 425 coincide with the CDRs or antigen-binding site. For these analysis comparative inhibition-biding curves were performed with the murine (FIG. 2A) and humanized (FIG. 2B) version of 425 mAb by indirect ELISA using A431 cells. All three Anti-Ids can inhibit binding of both versions of 425, each Ab2 has similar inhibition-binding curves showing that the 425 idiotopes recognized by 5A6, 3B6 and 15H8 are directly implicated in antigen recognition. 15H8 was 10 times more effective to inhibit 425-A431 cell binding than 5A6 and 3B6. The dissociation constant (KD) of Anti-Ids was calculated to determine the degree of fit of Ab2 to 425 paratope, KD constant of each Ab2 is given in Table I, 15H8 has more affinity with 425 correlating with its higher capacity to inhibit EGFR425 binding. These results also suggest that at least two different idiotopes on mAb425 are recognized by Anti-Ids.

TABLE I

| Ab2  | KD              |
|------|-----------------|
| 5A6  | $1.002 \cdot 10^{-9}$ M |
| 3B6  | $1.25 \cdot 10^{-9}$ M  |
| 15H8 | $0.3 \cdot 10^{-9}$ M   |

Syngeneic (Balb/c), allogeneic (B6D2F1) and xenogeneic (rat, rabbit) Ab3 induction.

The usefulness of this Ab2 as Id vaccines has been evaluated analyzing their immunogenicity. True internal image Ab2 should be able to induce Ab3 with Ab1-like specificity, crossing the species barrier. Ab3 were generated in mice, rats and rabbits following immunizing protocols described below, e.g., Example 7. Anti-anti-Id antibodies were detectable 2 weeks after the first does and reached the maximum level 6–8 weeks after the first dose was given. Specific response against immunizing Ab2 was maintained for up to 12 months in rats and rabbits while it was transient in mice decreasing Ab3 titre in the next months. All rabbit generated Anti-murine Igs; Ab3 sera titre against immunizing Ab2 was 5–10 times higher than those found against isotype and allotype matched Igs, indicating that the immune response against the constant region of Ab2 does not disturb the immune response against V region.

To determine an effective immunization against those Ab2 determinants which make contact with mAb 425 paratope (where the antigen-mimicking idiotypes should be located), an inhibition binding assay was performed in which the binding of 5A6, 3B6 or 15H8 Ab2 to mAb 425 was measured in presence of serial dilutions of Ab3 sera from animals immunized with Ab2 or unrelated murine mAbs. In Table II, the Ab3 sera dilution which produces 100% Ab2-Ab1 binding inhibition is given from Balb/c mice (A), rabbits (B) and rats (C). As shown in Table II A,B and C, all anti-5A6 Ab3 sera raised in the 3 species inhibited: 5A6and 3B6 mAb-425 binding with the same efficiency, Anti-3B6 sera showed similar inhibition patterns suggesting that both anti-Ids may have shared idiotypes. Furthermore, some rat and murine Anti-15H8 sera were found to inhibit 5A6 and 3B6 to 425 binding suggesting a partial idiotypic identity. Such reactivities were not detected in Anti-15H8 rabbit sera suggesting that Ab3 response in rabbits can be mainly directed against other more immunodominant idiotypes, this possibility is also supported by the finding of higher inhibiting titres in rabbit Ab3 sera than those found in rats and mice.

The antigenic identity between 5A6 and 3B6 was studied in a competitive ELISA, serial dilutions ($10^{-3}$ to $10^{-5}$) of rabbit and rat Ab3 sera were tested for Ab2 binding in presence of an equal volume (1 mg/ml) of Ab2 or control mAbs. Inhibition binding curves corresponding to rat Ab3 sera are shown in FIG. 3. 5A6 and 3B6 generate identical Ab3 repertoire in rats and rabbits: Anti-5A6 sera reacts equally well with 5A6 or 3B6 Ab2 coated on ELISA plates and are equally inhibited by both Ab2. Rabbit Ab3 sera had similar pattern of inhibition to those shown if FIG 3 for rat sera.

TABLE II A

| | Ab2-mAB 425 inhibition Binding | | |
|---|---|---|---|
| Balb/c Ab3 | 5A6 | 3B6 | 15H8 |
| 5A6 | 1/600 | 1/600 | — |
|  | 1/1200 | 1/1200 | 1/150 |
|  | 1/300 | 1/300 | — |
|  | 1/4800 | 1/2400 | 1/75 |
|  | 1/4800 | 1/4800 | 1/150 |
| 3B6 | 1/6400 | 1/6400 | — |
|  | 1/2400 | 1/2400 | — |
|  | 1/4800 | 1/4800 | — |
|  | 1/800 | 1/800 | — |
|  | 1/4800 | 1/4800 | — |
| 15H8 | — | — | 1/9600 |
|  | — | — | 1/9600 |
|  | — | — | 1/9600 |
|  | — | — | 1/9600 |
|  | 1/2400 | 1/2400 | 1/9600 |
| F111 | — | — | — |
|  | — | — | — |
| KLH | — | — | — |
|  | — | — | — |
|  | — | — | — |
| Preinmune sera | — | — | — |

TABLE II B

| | Ab2-mAb 425 inhibition binding | | |
|---|---|---|---|
| Rabbit Ab3 | 5A6 | 3B6 | 15H8 |
| 5A6 | 1/3200 | 1/3200 | — |
|  | 1/12800 | 1/12800 | — |
|  | 1/6400 | 1/12800 | — |
|  | 1/12800 | 1/6400 | — |
|  | 1/12800 | 1/12800 | — |
| 3B6 | 1/6400 | 1/6400 | — |
|  | 1/3200 | 1/6400 | — |
|  | 1/12800 | 1/12800 | — |
|  | 1/12800 | 1/12800 | — |
|  | 1/12800 | 1/12800 | — |
| 15H8 | — | — | 1/12800 |
|  | — | — | 1/12800 |
|  | — | — | 1/1600 |
|  | — | — | 1/3200 |
| mAb15 | — | — | ND |
| F111 | — | — | — |
| mAb425 | — | — | — |
| KLH | — | — | — |
| Preinmune- sera | — | — | — |

TABLE II C

| | Ab2-mAB 425 Inhibition binding | | |
|---|---|---|---|
| Rat Ab3 | 5A6 | 3B6 | 15H8 |
| 5A6 | 1/2400 | 1/4800 | — |
|  | 1/2400 | 1/2400 | — |
| 3B6 | 1/2560 | 1/2560 | — |
|  | 1/1280 | 1/2560 | — |
| 15H8 | 1/160 | 1/320 | 1/2560 |
|  | — | — | 1/1280 |
| F111 | — | — | — |
| MAB15 | — | — | — |
| KLH | — | — | — |

TABLE II C-continued

| | Ab2-mAB 425 Inhibition binding | | |
|---|---|---|---|
| Rat Ab3 | 5A6 | 3B6 | 15H8 |
| Preinmune-sera | — | — | — |

Identification of Anti-EGFR Ab3 antibodies.

Anti receptor antibodies were detected in Ab3 sera by direct immunofluorescence against A43 1 and C33A cells, and results are shown in Table III:

TABLE III

| | Immuno-fluoresoence | | ELISA | |
|---|---|---|---|---|
| Ab[c] | A431 | C33[a] | A431 | sEGFr[b] |
| Anti-5A6 | 7/14 | 0/14 | 6/14 | 5/15 |
| Anti-3B6 | 10/13 | 0/13 | 6/13 | 5/16 |
| Anti-15H8 | 4/12 | 0/12 | 0/12 | 0/11 |
| Anti-mAb15 | 0/2 | 0/2 | 0/2 | 0/4 |
| Anti-R24 | 0/3 | 0/3 | 0/3 | 0/3 |
| KLH | 0/5 | 0/5 | 0/5 | 0/4 |
| Preimmune | 0/20 | 0/20 | 0/20 | NT |

Anti-Id vaccination in murine system induces the formation of Anti-EGFR antibodies, however no Anti-EGFR antibodies could be detected in Ab3 from rats and rabbits. The development of Anti-EGFR antibodies in B6D2F1 mice confirms that Ab2 vaccination is not genetically restricted to murine Balb/c strain. Specific antibodies reached titres 1/50–1/1600 when tested against sEGFR by ELISA.

Ab3-EGFR inhibition binding by 5A6, 3B6 and 15H8.

These assays were performed to test if Anti-Ids mirnick in a three-dimensional fashion the EGFR Different dilutions of Anti-EGFR Ab3 sera from Balb/c and B6D2F1 mice were mixed with Anbti-Ids and left react 4 hours room temperature, then, they were tested for anti-receptor antibodies with sEGFR coated plates and the percentage of inhibition calculated from OD values is shown in FIG. 4. 5A6 and 3B6 gives 100% inhibition indicating that they share the three-dimensional structure of the original antigen. 15H8 gave 15–35% inhibition of Anti-EGFR Ab3 from 5A6 or 3B6.

It has been claimed that true internal image Anti-Ids can subtitute the immunogenic properties of antigen and induce specific response in different species, this is not the case of 5A6 and 3B6 that fails to induce Anti-EGFR in rats and rabbits; the serologic assays performed suggest, however, that the anti-receptor antibodies detected in mice are induced by 5A6 and 3B6 idiotype determinants resembling EGFR.

Primary structures of Ab2 and comparison of amino acid sequences with EGFR. DNA sequencing has been performed to analyze the structural basis of their immunogenic properties. The VH and VL sequences of 5A6, 3B6 and 15H8 are displayed in FIG. 5 (SEQ ID NOS: 1–12). The amino acid sequences of VH regions were classified into subgroup IIID according to Kabat. VL regions of 5A6 and 15H8 belong to kV group and 3B6 to kIII according to Kabat. CDR sequences were compared with amino acid sequences of human EGFR (GQHUE from SPIRS data bank), (FIG. 6). Maximum homology was found between residues 77–84 from CDR2H and residues 125–129 from CDR3H and 70–76 from 5A6 and 74–80 CDR2L, the highest homologous CGFR regions, amino acid 437–452 and 492–502 with CDR3H are located in the hypothetical ligand-binding domains of receptor protein described by A. Ulllrich et al. (1987), Nature, 309:416. 15H8 shares identical CDR2H sequence but has different CDR3H and CDR2L sequences. To analyze which role each homologous CDR plays in the formation of internal image EGFR, we have compared 5A6 and 3B6 sequences with known VH and VL regions compiled by Kabat. Some of the VH chains according to the invention are found to be highly homologous to 5A6 and 3B6, they show similar CDR1H and CDR2H, suggesting that CDR3H sequences play the main role in 425-paratope recognition and EGFR mimicry. It was found that there are 63 Igs (mainly from murine of human origin) with CDR3H regions partially homologous (50–87%) to CDR3H from 5A6 and 3B6. Homologous amino acid appear accumulated at residues 100H-102 while less homologous amino acid have been found along GYVG (amino acids 1–4 of SEQ ID NO: 13) segment where the maximum homology with EGFR has been found. No antibody from murine or human origin has been found to posses the residue V at position 100D which is exclusive of 5A6, 3B6. VL 5A6 and 3B6 show homologies with murine Kappa chains, completely different VL chain sequences have the same specificity The role of CDR2L seems to be not related to a strict amino acid identity. 5A6, 3B6 have different sequences constructing an identical EGFR internal image structure, however amino acid homologies with EGFR appear accumulated in this region.

To evaluate its immunological effect as Id vaccines, we have analyzed the accessibility and antigenic properties of CDR2H, CDR3H and CDR2L regions. The antigenic index (a measure of antigenic probability) was calculated from ANTIGENIC program, the secondary structure was defined by DSSP program in order to determine the accessibility of the homologous sequences found.

Secondary and primary structure analysis reveals that these homologous residues are accessible and also coincide with regions showing positive antigenic index, therefore they can be directly implicated in the anti-internal image response. VL5A6 and VL3B6 chains present 7 non-identical antigenic regions and 11024 and 11603 angstroms of accessible surface protein respectively, able to constitute antigenic idiotopes, however both antibodies generate identical Ab3 response in mice, rabbits and rats. These results suggest that the Anti-Anti-Id response found in this system is exclusively directed to Id defined by VH chains of 5A6 and 3B6.

As the immunological and structural analysis of 5A6 and 3B6 Anti-Ids shows that they are the internal image of EGFR external domain, we have analyzed why they fail to induce response in a second specie. The positive antigenic GYVGYAIDY (SEQ ID NO:13) CDR3H region carrying the EGFR equivalent GYVGY (amino acids 1–5 of SEQ ID NO: 13) segments, were compared with CDR3H sequences from murine, rat and rabbit antibodies. A large group of murine antibodies have the sequence YAIDY (amino acids 5–9 of SEQ ID NO:13), so among the predicted antigenic region on CDR3H, the residues GYVG (amino acids 1–4 of SEQ ID NO:13) are expected to define a private idiotope immunogenic in mice. No rabbit Ig has found to posses YAIDY (amino acids 5–9 of SEQ ID NO:13) sequence, being possible that rabbit Anti-Anti-Id response is directed against other idiotopes defined by larger antigenic regions, spoiling the anti-internal image response.

In summary, the present invention discloses the following:

In the active immunotherapy of cancer different aproaches have been used. Anti-idiotypic antibodies mimicking the immunological effect of tumor markers have been applied in cancer patients to obtain an specific anti-tumor response regulated by Id-Anti-Id interactions.

Anti-Id mAbs directed against mAb 425 have been obtained to develop specific vaccines for EGFR Three antibodies (5A6, 3B6 and 15H8) have been selected recognizing combining-site associated idiotopes on mAb425 defined by their CDR sequences as demonstrated by inhibition binding of humanized version of 425 mAb to EGFR.

Immunological and serological assays have shown that 5A6 and 3B6 act as internal images inducing a specific humoral response in mice. Ab1-like antibodies from Ab3 sera binds to membrane-bound EGFR on A431 cells and reacts against sEGFR. The reaction is completely inhibited by both 5A6 and 3B6 Ab2 (independenly of the Anti-Id used for the immunization), suggesting that 5A6 and 3B6 carry the same internal image of EGFR Immunological data suggest partial idiotypic sharing with the internal image idiotype of 5A6 and 3B6 and 425 paratope-related Id from 15H8, serologic assays have shown partial inhibition binding of Anti-5A6 and Anti-3B6 murine Ab3 to Ab2 or EGFR in the presence of 15H8. Immunological studies have revealed the lack of biological effect: IgM antibodies (reacting with A431 cells but failing to recognize sEGFR) have been induced, however they are not inhibited by 15H8. These results suggest that unspecific clones have been activated during the immunization protocols.

The investigation of structural correlation between Id and antigen have been performed to know what structures in the Anti-Ids are implicated in the generation of Anti-EGFR response.

After sequencing 5A6, 3B6 and 15H8 and comparing amino acid homologies with the EGFR, we have found a set of homologous and equivalent amino-acid in the antigenic and accesible regions of CDR2H, CDR3H and CDR2L These data are in agreement with several reports demostrating the presence of homologous sequences in the CDRs (or adjacent regions) from VL and VH chains that participate in the structural formation of internal image bearing idiotypes (31–33). The finding that different sequences in 5A6 and 3B6, constructs two antibodies with identical immunological effect, has allowed us to analyze the role of CDRs and framework regions in the induction of Ab3 response and in the conformation of internal image of EGFR.

CDR2L, CDR2H and CDR3H from 5A6 and 3B6 are probably implicated in the construction of the internal image because maximum homologies and equivalent amino acid have been found with EGFR external domain in this regions. A three-dimensional mimicry seems play a main role as deduced by the following findings a) CDR2L from 5A6 and 3B6 are different, but give rise to identical Anti-EGFR response.
b) Homologous residues from CDR2H have been found in non-related antibodies, so their participation in the internal image structure is not dependent of an exclusive linear identity.
c) The affinities found between CDRs and residues 148–154, 437–452 and 492–502 from EGFR are mainly based on equivalent amino acid.
d) Equivalent amino acid accumulate in those CDRs but not in other regions.

The idiotypic analysis of several families of antibodies (Anti-PC, Anti-dextran, Anti-galactan, Anti-NIP antibodies) have shown that in an antigen driven system, the expression of Ids involve a minimun of amino acid from CDR2H, CDR3H and a pairing with specific L chains. Our immunologic and sequencing data suggest that we have generated an Ab1-Ab2-Ab3 Id cascade restricted to a limited set of idiotypic regions defined by 425-paratope and Ab2-paratope. The most important feature has been to obtain two Ab2s, 5A6 and 3B6 showing identic immunologic properties (and thus idiotypic determinants) originated from identical VH chains paired to different VL chains.

The biological effectiveness of Anti-Id antibodies correlates with their affinity with the idiotypic repertoire in the receptor specie. The analysis of residues implicated in the formation of 5A6 and 3B6 internal image structure have shown them included in a larger antigenic region (residues 100F-101 in H chain) found to be homologous to other murine antibodies (from NBRF protein Database) but not in rabbits. Thus internal image structure determines an idiotype "seen" by the murine immune system but masked in a larger idiotypic region when administered in rabbits. This hypothesis is also supported by the immunological results: Anti-5A6 and Anti-3B6 paratope-related Ab3 sera titres are higher in rabbits than in mice. Homologous 100F-101 residues have been also found to be present in human antibodies (from NBRF Database), indicating the effectiveness of internal image 5A6 and 3B6 in human systems. The effectiveness of internal image antiidiotypic antibodies as vaccines has been demonstrated in various animal models and in clinical trials. The obtention of anti-Ids recognizing Anti-EGF antibodies have been recently reported by Suarez (Suarez, E. et al., 1993, *Immunologia* 12:122), who obtained 4 non-internal image mAbs.

5A6 and 3B6 are the first Internal image Anti-Id mAbs reported mimicking the External Domain of human EGFR. The biological characteristics of mAb 425, determines that 5A6 and 3B6 mimic the ligand-binding site of EGFR.

Serological studies, biological effect in animal models, and structural analysis suggest their potential value in human vaccination

THERAPEUTIC AND DIAGNOSTIC USE

The antibodies according to the invention are administered to human and non-human mammal patients for therapy. Therefore, it is an object of the invention to provide a pharmaceutical formulation comprising as active ingredient at least one antibody or antibody fragment as defined herein, associated with one or more pharmaceutically acceptable carrier, excipient or diluent therefore.

Typically, the antibodies of this invention are injected intravenously or parenterally. Generally, the dosage ranges for the administration of the antibodies fragments are large enough to produce the desired tumor suppressing and tumor lysing effect. The dosage will depend on age, condition, sex and extent of the disease in the patient and can vary from 0.1 mg/kg to 200 mg/kg, preferably from 0.1 mg/kg to 100 mg/kg/dose in one or more doses administered daily, for one or several days, or as such to elicit an effective immune response.

Preparations for parenteral administration includes sterile aqueous or non-aqueous solutions, suspensions, and emulsions. Examples of non-aqueous solvents are propylene glycol polyethylene glycol vegetable oils such as olive oils, and injectable organic esters such as ethyl oleate and other solvents known in the art which are suitable for these purposes. The antibodies of this invention can be used in a composition comprising a physiologically acceptable carrier. Examples of such suitable carriers are saline, PBS, Ringer's solution, or lactated Ringer's solution. Preservatives and other additives such as antibiotics, antioxidants, and chelating agents may also be present in the pharmaceutical formulations.

The antibody (or, optionally, the antibody fragment) can also be conjugated according to known methods to cytokines such as IL-2 in order to support their cytotoxicity.

The pharmaceutical formulations of the present invention are suitable for the treatment of all kinds of tumors, including melanomas, gliomas and carcinomas, as well as tumors of the circulating system and solid tumors. For diagnostic purposes the antibody can be conjugated, for example, to a radio-opaque dye or can be radiolabelled. A preferred labelling method is the Iodogen method. Preferably the antibody will be administered as F(ab')$_2$ or scFv fragments for diagnostic purposes. This provides superior results so that background substraction is unnecessary.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patent and publications cited above and below, and of corresponding European application 95107967.2, are hereby incorporated by reference.

EXAMPLES

Example (1)

Humanized mAb 425

The Humanization of mAb 425 has been previously described (Kettleborough,C. A. et al.,1991, *Protein Eng.* 4:773). The reshaped form of mAb425 contains the murine CDRs grafted in human variable regions keeping the antigen binding site structure. It has been used to define more precisely the localization of 425 idiotypes recognized by the Ab2.

Example (2)

Production of Anti-idiotypic mAbs to Anti-EGFR 425 mAb

Balb/c mice were primed with i.p. injection of 75 mg. of purified 425 mAb coupled to KLH (Sigma), polymerized with glutaraldehide and mixed with CFA (Difco). Animals were boosted at days 7, 14, 21, 28 and 38 with the same immunogen emulsified with IFA. Fusion was done 3 days after the last boost Spleen cells from immunized mice where fused with HL1-Friendly Myeloma-653 using 1450 polyethylenglycol (Boehringer Mannheim), following a protocol previously described (Carceller, A.,1988,. *Sangre* 33(3) :220). Fused cells were grown in 39% RPMI 1640, 39% Hybridoma Medium (Gibco), 20% Fetal Calf Serum and 2% HAT. Positive hybrids were cloned three times by limiting dilution.

Example (3)

Detection and Analysis of Ab2 Activity

Anti-idiotypic antibodies were detected by sandwich ELISA with polystyrene microtiter plates (Nunc, Maxisorb) coated with 1 mg./ml. of purified 425 mAb. Plates were blocked by 2% BSA-PBS and crude supernatants or diluted sera in 0,2% BSA-PBS were incubated overnight at 4. After washing with PBS-0.05% Tween 20, biotinylated mAb 425, prepared by the method of Harlow and Lane (1988), *Antibodies: A Laboratory Manual,* was added for 1 h. 37° C., plates were washed three times and HRPO-streptavidin (Dako) diluted 1/1000 in 2% BSA-PBS was added. 3-3-5-5 tetramethyl benzidine (Sigma) solution was used as substrate. OD was measured at 450 mm.

Example (4)

Dissociation Constant (KD) of 5A6, 3B6 and H8 Ab2 mAbs

This determination was done according to the method of Friguet (Friguet,B. et al., 1985, *J.Immunol.Methods* 77:305), briefly: serial dilutions of mAb425 ($2.10^{-8}$M to $2.10^{-11}$M) were incubated with fixed concentrations of Ab2 until equilibrium was reached. The concentration of free Ab2 was measured by indirect ELISA using microtiter plates coated with 1 mg./ml. of mAb 425 and RPO-Rabbit Anti-murine IgG1 (Zymed).

Example (5)

Purified Human EGFR External Domain (sEGFR)

The purification of external domain of human EGFR and the immunoaffinity chromatography from EGFR secreted by A431 cells has been previously reported (Weber,W. et al., 1984, *J.Biol. Chem.* 259 (23):14631). It was used to confirm the specificity of Ab3 by indirect and competitive assays.

Example (6)

Assays for Localization of Idiotypes Recognized in 425 mAb

To localize 425 idiotypes defined by 5A6, 3B6 and 15H8, they were tested for their ability to inhibit 425-EGFR binding. This analysis was first performed with purified sEGFR Crude supernatants and 50 mg./ml. of purified Ab2 were mixed with 125 ng. of mAb 425. After 4h incubation at 37° C., 425 activity was tested by ELISA using microtiter plates coated with 2,5mg./ml. of sEGFR. Plates were washed three times with PBS-1% BSA and AP-rabbit Antimouse Igs (Dako) was added. 3,3,5,5, tetramethilbenzidine was used as substrate and OD at 405nm. was recorded in a Titertek Multiscn plate reader.

These analysis were complemented by comparing their inhibition binding curves of murine and reshaped 425: 100 ng./ml. of murine or reshaped 425 were mixed with equal volumes of increasing concentrations ($2.10^{-2}$M to $2.10^{1}$M ) of purified 5A6, 3B6, 15H8 Ab2s or unrelated murine IgG1 antibodies. Remaining activity was tested by indirect Cel-lELISA against A431 cells, previously fixed in microtiter plate ($5.10^5$/well) with 0,1% glutardaldehyde. After 60'incubation at 37° C., cells were washed 3 times with PBS-1% BSA-0,05% Tween 20. HRPO-Goat-Anti murine IgG2a (Dianova) and HRPO-Goat Anti-human IgG was used respectively to detect bound Ab1, orthophenyldiamide (Sigma) was used as substrate.

Example (7)

Ab3 Generation in Syngeneic (Balb/c Mice), Allogeneic (F6D2F1 Mice) and Xenogeneic (Wistar rat and NZW Rabbits) System and Ab3 Detection Purified Ab2s were coupled to KLH (Calbiochem) by glutaraldehyde (Sigma) and emulsified with CFA or IFA.

Animals were administered at days 0, 15, 30 and 60. In some assays, additional boosters were performed 8–12 months later to study the stability of Ab3 response. Animals received at each dose 75 mg (mice), 150 mg (rats) and 300 mg (rabbits) of total Ig by intraperitoneal inoculation (mice) or subcutaneously at different sites (rats and rabbits). Control groups received same doses of irrelevant KLH-coupled murine Igs or KLH alone. Blood samples were collected at day 0 and 1 week after each boost Serial serum dilutions (in PBS-0, 15% dry milk) were added to microtiter plates coated previously with 1 mg/ml. of Ab2 or other murine Igs. Bound anti-anti-ids were detected with biotinylated Ab2 (in murine Ab3 sera), HRPO Rabbit-Anti Rat Igs (Dako) deprived for cross-reactivity against murine Igs and HRPO Swine Anti-Rabbit Igs (Dako). Anti-isotypic and allotypic antibodies developed in rats and rabbits were eliminated with extensive adsorption of 1150-1/100 diluted sera samples with murine IgG1 after incubation overnight at 4.

Example (8)

Ab2–Ab1 Inhibition Binding by Ab3 Sera

This assay was done to detect antibodies reacting with those Ab2 sites that make contact with mAb 425-paratope. Briefly, 8–16 ng./ml purified 5A6, 3B6, 15H8 and F111 were mixed with serial dilutions of Ab3 containing sera, after overnight incubation at 4° C., remaining Ab2 activity was detected by direct ELISA against 1 mg./ml of 425 coated on polystyrene plates. Bound Ab2 was detected with PA-Rabbit Anti-mouse IgG1 (Zymed).

Example (9)

Determination of Ab2 Idiotypic Identity by Mutual Competition for Ab3 Binding To determine idiotypic identity between each anti-id antibody, Ab2 were tested for binding inhibition of Ab3 sera to Ab2-coated plates.Serial dilutions of rat Ab3 sera ($10^{-3}$ to $10^{-5}$) were tested for Ab2 binding in presence of an equal volume (1 mg./ml.) of Ab2 or control mAbs previously incubated overnight at 4°.

Example (10)

Detection of Anti-EGFR Antibodies within Ab3 Response

Murine, rat and rabbit Ab3 sera was tested for Ab1-like activity using CellELISA against A431 cells as described before, or by direct ELISA with sEGFR (2,5 mg./ml.). HRPO Rabbit Anti-mouse Igs (Dako), Rabbit Anti-Rat Igs (Dako) and Swine Anti-Rabbit Igs (Dako) were used respectively as second antibody. Anti-receptor antibodies were also tested by direct immunofluorescence assay using unfixed, live A431 cells, cultured in Terasali plates.

Example (11)

EGFR-Ab3 Inhibition Binding by 5A6, 3B6 and 15H8 Anti-Ids

Sharing determinants between receptor and Anti-Ids were tested by competitive assay. 120–240 mg./ml. of 5A6, 3B6, 15H8 or unrelated IgGI were incubated overnight at 4° C. with ½s–⅟₁₅₀ dilutions of Ab3 Anti-EGFR sera and tested for Anti-receptor activity by ELISA, CellELISA and direct immunofluorescent assays. The percentage of inhibition was calculated as follows:

$$\% \text{ Inhibition} = 1 - \left( \frac{\text{OD with Ab2} - \text{OD background}}{\text{OD without Ab2} - \text{OD background}} \right) - 100$$

Example (12)

RNA and cDNA Preparation

Total RNA was isolated from 5A6, 3B6 and 15H8 hybridoma cell lines. PBS-washed cells were suspended in guanidinium thiocyanate solution and the RNA was isolated using a cesium chloride gradient ultracentrifugation method from Chirgwin (Chirgwin et al., 1979, *Biochemistry* 18, 5294). First-stranded cDNA was synthesized using a Pharmacia kit. The synthesis was done in 15 μl with 5 μg of RNA, during one hour at 37° C. First strand cDNA was used directly form amplification without previous cloning.

Example (13)

PCR Amplification

A set of PCR primers were used to amplify copies of the mouse light chain variable regions and mouse heavy chain variable regions. The 5' primers, were designed to hybridize to the leader sequence. Primers were a mixture of 61 oligonucleotides, for the heavy chain variable domain, and 405 oligonucleotides, for the kappa chain variable domain. 3' primers were designed to anneal to the constant region. A specific IgG1 and kappa mouse primers were used.

For amplification, with a thermostable DNA polymerase, 25 μl reaction mixture containing: 1 μl of the cDNA-RNA hybrid, 250 nM of the appropriate 5' and 3' primers mixture, 200 mM of each DNTP, 1 mM $MgCl_2$ (for the light chain), 2 mM $MgCl_2$ (for the heavy chain), and 1 U of Taq polymerase (Cetus), was overlaid with mineral oil and subjected to a touchdown starting with a 60° C. until 55° C. of annealing temperature. One tenth of the PCR reaction was run on a 1% agarose TAE gel electrophoresis and ethidium bromide-stained to visualize the resulting PCR products.

Example (14)

Molecular Cloning and Sequencing

1 λl of each PCR-product was ligated into TA vector (Invitrogen, San Diego). The DNA ligation reactions, for VH and VL chain regions of each Ab2, were transformed by a Heat-Shock into competent TG1 *E.coli* cells. This created six DNA libraries, one from light variable regions and the others from heavy variable regions of each mAb. Colonies were selected on LB plates with 100 μg/ml carbenicilin and some were toothepicked for further analysis. Positive colonies were detected by PCR screening or using plasmid digestion as described by Güssow (Güssow, D., Clackson T., 1989 T; Nucleic Acids Res. 17: 4000). Double-stranded plasmidic DNA was prepared (Wizard preps, Promega Corp.) for sequencing from transformants. Dideoxy-nucleotide chain termination, following the methodology from Sanger et al. (Sanger, F. et al., 1977, Proc. Nat.Acad. Sci. U.S.A 74: 5463) was carried out using Taq polimerase. Primers used in the sequencing reactions annealed in TA vector.

Example (15)

Computer Analysis and Sequence Comparison

The software program DSSP (Sybil) was used to calculate the secondary structure of Ab2 and their accessible residues.

ANTIGENIC was used to predict the antigenic regions using the method of Kolaskar and Tongaonkar (Kolaskar,A. S. et al.,1990, FEBS-Lett 276(1–2):172). Ab2 and EGFR homologies were defined by BESTFIT program using Gencore disk for symbol comparison table. Compared human EGFR sequence was those reported earlier (Ullrich et al., 1984, Nature 309:418). Ab2 were compared with other known Igs using the Protein Identification Resource (PIR) data bank compiled by National Biomedical Research Fundation (NBRF) and PROSIS program The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. An isolated monoclonal true internal image anti-idiotypic antibody (Ab2) containing antigen recognition sites which mimic antigenic regions of epidermal growth factor receptor (EGFR) and thereby induce an immune response against EGFR when administered to a host, obtained from a murine hybridoma produced by fusing mouse splenocytes immunized with idiotypic (Ab1) murine Mab 425 (ATCC HB 9629) with myeloma cells, wherein the CDR regions and the FR regions of said anti-idiotypic antibody comprise an amino acid sequence selected from SEQ ID NO:2, 4, 6, 8, 10 or 12, or a humanized or chimeric antibody thereof.

2. An isolated monoclonal true internal image anti-idiotypic antibody (Ab2) containing antigen recognition sites which mimic antigenic regions of epidermal growth factor receptor (EGFR) and thereby induce an immune response against EGFR when administered to a host, obtained from a murine hybridoma produced by fusing mouse splenocytes immunized with idiotypic (Ab1) murine Mab 425 (ATCC HB 9629), with myeloma cells, comprising an amino acid sequence coding for the CDR and FR regions of said anti-idiotypic antibody encoded by a nucleotide sequence selected from SEQ ID NO: 1, 3, 5, 7, 9 or 11, or humanized or chimeric antibody thereof.

3. A monoclonal anti-idiotypic antibody of claim 1, wherein the CDR regions and the FR regions of said antibody comprise an amino acid sequence selected from SEQ ID NO:6, 8, 10 or 12.

4. A monoclonal anti-idiotypic antibody of claim 2, comprising an amino acid sequence coding for the CDR and FR regions of said antibody encoded by a nucleotide sequence selected from SEQ ID NO: 5, 7, 9 or 11.

5. A composition comprising a monoclonal antibody of claim 1 and a pharmaceutically acceptable carrier.

6. A composition comprising a monoclonal antibody of claim 2 and a pharmaceutically acceptable carrier.

7. A composition comprising a monoclonal antibody of claim 3 and a pharmaceutically acceptable carrier.

8. A composition comprising a monoclonal antibody of claim 4 and a pharmaceutically acceptable carrier.

* * * * *

SEQUENCE LISTING

```
(1) GENERAL INFORMATION:

(iii) NUMBER OF SEQUENCES: 13

(2) INFORMATION FOR SEQ ID NO: 1:

(i) SEQUENCE CHARACTERISTICS:
            (A) LENGTH: 477 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
            (A) ORGANISM: monoclonal anti-EGFR anti-idiotypic antibodxy
            (C) INDIVIDUAL ISOLATE: 15H8- heavy chain (ix) FEATURE:
            (A) NAME/KEY: CDS
            (B) LOCATION:1..477

(xi) SEQUENCE DESCRIPTION: SEQ ID NO: 1:

ATG GAC TCC AGG CTC AAT TTA GTT TTC CTT GTC CTT GTT TTG AAA GGT        48
Met Asp Ser Arg Leu Asn Leu Val Phe Leu Val Leu Val Leu Lys Gly
 1               5                  10                  15

GTC CAG TGT GAA GTG CAA CTG GTG GAG TCT GGG GGA GGC TTA GTG AAG        96
Val Gln Cys Glu Val Gln Leu Val Glu Ser Gly Gly Gly Leu Val Lys
                20                  25                  30

CCT GGA GGG TCC CTG AAA CTC TCC TGT GCA GCC TCT GGA TTC ACT TTC       144
Pro Gly Gly Ser Leu Lys Leu Ser Cys Ala Ala Ser Gly Phe Thr Phe
            35                  40                  45

AGT GAC TAT TAC ATG TAT TGG TTT CGC CAG CAT CCG GGA AAG AGG CTG       192
Ser Asp Tyr Tyr Met Tyr Trp Phe Arg Gln His Pro Gly Lys Arg Leu
 50                  55                  60

GAG TGG GTC GCA ACC ATT AGT GAT GCT GGT ACT TAC ACC TAC TAT CCA       240
Glu Trp Val Ala Thr Ile Ser Asp Ala Gly Thr Tyr Thr Tyr Tyr Pro
 65                  70                  75                  80

GAC AGT CTG AAG GGG CGA TTC ACC ATC TCC AGA GAC AAT GCC AAG AAC       288
Asp Ser Leu Lys Gly Arg Phe Thr Ile Ser Arg Asp Asn Ala Lys Asn
                85                  90                  95

AAC CTG TAC CTC CAA ATG AGC AGT CTG AAG TCT GAG GAC ACA GCC ATG       336
Asn Leu Tyr Leu Gln Met Ser Ser Leu Lys Ser Glu Asp Thr Ala Met
            100                 105                 110

TAT TTC TGT GCA AGA GAC GGG GCA GCT CGG ACT TCG TCC CAG GTT TAT       384
Tyr Phe Cys Ala Arg Asp Gly Ala Ala Arg Thr Ser Ser Gln Val Tyr
            115                 120                 125

TAC TAT GGT ATG GAC TAC TGG GGT CAA GGA ACC TCA GTC ACC GTC TCC       432
```

```
Tyr Tyr Gly Met Asp Tyr Trp Gly Gln Gly Thr Ser Val Thr Val Ser
    130                 135                 140

TCA GCC AAA ACG ACA CCC CCA TCT GTC TAT CCA TTC CCG GGT TCC           477
Ser Ala Lys Thr Thr Pro Pro Ser Val Tyr Pro Phe Pro Gly Ser
145                 150                 155
```

(2) INFORMATION FOR SEQ ID NO: 2:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Asp Ser Arg Leu Asn Leu Val Phe Leu Val Leu Val Leu Lys Gly
 1               5                  10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
         35                  40                  45

Ser Asp Tyr Tyr Met Tyr Trp Phe Arg Gln His Pro Gly Lys Arg Leu
 50                  55                  60

Glu Trp Val Ala Thr Ile Ser Asp Ala Gly Thr Tyr Thr Tyr Tyr Pro
65                  70                  75                  80

Asp Ser Leu Lys Gly Arg Phe Thr Ile Ser Arg Asp Asn Ala Lys Asn
                85                  90                  95

Asn Leu Tyr Leu Gln Met Ser Ser Leu Lys Ser Glu Asp Thr Ala Met
                100                 105                 110

Tyr Phe Cys Ala Arg Asp Gly Ala Ala Arg Thr Ser Ser Gln Val Tyr
            115                 120                 125

Tyr Tyr Gly Met Asp Tyr Trp Gly Gln Gly Thr Ser Val Thr Val Ser
    130                 135                 140

Ser Ala Lys Thr Thr Pro Pro Ser Val Tyr Pro Phe Pro Gly Ser
145                 150                 155
```

(2) INFORMATION FOR SEQ ID NO: 3:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: monoclonal anti-idiotypic anti-EGFR antibody
        (C) INDIVIDUAL ISOLATE: 15H8 light chain (ix) FEATURE:
        (A) NAME/KEY: CDS
        (B) LOCATION: 1..441

(xi) SEQUENCE DESCRIPTION: SEQ ID NO: 3:

```
ATG GGC TTC AAG ATG GAG TCA CAT ATT CAG GTC TTT GTA TTC GTG TTG      48
Met Gly Phe Lys Met Glu Ser His Ile Gln Val Phe Val Phe Val Leu
160                 165                 170                 175
```

```
CTC TGG TTG TCT GGT GTT GAT GGA GAC ATT GTG ATG ACC CAG TCT CAA    96
Leu Trp Leu Ser Gly Val Asp Gly Asp Ile Val Met Thr Gln Ser Gln
            180                     185                 190

AAA TTC ATG TCC ACA TCA GTA GGA GAC AGG GTC AGC ATC ACC TGC AAG   144
Lys Phe Met Ser Thr Ser Val Gly Asp Arg Val Ser Ile Thr Cys Lys
            195                     200                 205

GCC AGT CAG AAT GTT CGT ACT GCT GTA GCC TGG TAT CAA CAG AAA CCA   192
Ala Ser Gln Asn Val Arg Thr Ala Val Ala Trp Tyr Gln Gln Lys Pro
            210                     215                 220

GGG CAG TCT CCT AAA GCA CTG ATT TAC TTG GCA TCC AAC CGG CAC ACT   240
Gly Gln Ser Pro Lys Ala Leu Ile Tyr Leu Ala Ser Asn Arg His Thr
            225                     230                 235

GGA GTC CCT GAT CGC TTC ACA GGC AGT GGA TCT GGG ACA GAT TTC ACT   288
Gly Val Pro Asp Arg Phe Thr Gly Ser Gly Ser Gly Thr Asp Phe Thr
240                     245                 250                 255

CTC ACC ATT AGC AAT GTG CAA TCT GAA GAC CTG GCA GAT TAT TTC TGT   336
Leu Thr Ile Ser Asn Val Gln Ser Glu Asp Leu Ala Asp Tyr Phe Cys
            260                     265                 270

CTG CAA CAT TGG AAT TAT CCT CTC ACG TTC GGC TCG GGG ACA AAG TTG   384
Leu Gln His Trp Asn Tyr Pro Leu Thr Phe Gly Ser Gly Thr Lys Leu
            275                     280                 285

GAA ATA AAA CGG GCT GAT GCT GCA CCA ACT GTA TCC ATC TTC CCA CCA   432
Glu Ile Lys Arg Ala Asp Ala Ala Pro Thr Val Ser Ile Phe Pro Pro
            290                     295                 300

TCC ACC CGG                                                       441
Ser Thr Arg
    305
```

(2) INFORMATION FOR SEQ ID NO: 4:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gly Phe Lys Met Glu Ser His Ile Gln Val Phe Val Phe Val Leu
 1               5                  10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Ile Thr Cys Lys
            35                  40                  45

Ala Ser Gln Asn Val Arg Thr Ala Val Ala Trp Tyr Gln Gln Lys Pro
    50                  55                  60

Gly Gln Ser Pro Lys Ala Leu Ile Tyr Leu Ala Ser Asn Arg His Thr
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Asp Tyr Phe Cys
            100                 105                 110

Leu Gln His Trp Asn Tyr Pro Leu Thr Phe Gly Ser Gly Thr Lys Leu
            115                 120                 125

Glu Ile Lys Arg Ala Asp Ala Ala Pro Thr Val Ser Ile Phe Pro Pro
            130                 135                 140

Ser Thr Arg
145
```

(2) INFORMATION FOR SEQ ID NO: 5:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: monoclonal anti-idiotypic anti-EGFR antibody
        (C) INDIVIDUAL ISOLATE: 5A6 heavy chain (ix) FEATURE:
        (A) NAME/KEY: CDS
        (B) LOCATION:1..474

(xi) SEQUENCE DESCRIPTION: SEQ ID NO: 5:

```
ATG GAC TTT GGG CTC AGC TTG ATT TTC CTT GTC CTT GTT TTT AAA GGT        48
Met Asp Phe Gly Leu Ser Leu Ile Phe Leu Val Leu Val Phe Lys Gly
        150                 155                 160

GTC CTG TGT GAC GTG AAG CTC GTG GAG TCT GGG GGA GGC TTA GTG AAG        96
Val Leu Cys Asp Val Lys Leu Val Glu Ser Gly Gly Gly Leu Val Lys
        165                 170                 175

CTT GGA GGG TCC CTG AAA CTA TCC TGT GCA GCC TCT GGA TTC ACT TTC       144
Leu Gly Gly Ser Leu Lys Leu Ser Cys Ala Ala Ser Gly Phe Thr Phe
180                 185                 190                 195

AGT AAC TAT TAC ATG TCT TGG GTT CGC CAG ACT CCA GAG AAG AGG CTG       192
Ser Asn Tyr Tyr Met Ser Trp Val Arg Gln Thr Pro Glu Lys Arg Leu
                200                 205                 210

GAG TTT GTC GCA GCC ATT AAT AGT AAT GGT GGT AGC ACC TAC TAT CCA       240
Glu Phe Val Ala Ala Ile Asn Ser Asn Gly Gly Ser Thr Tyr Tyr Pro
                215                 220                 225

GAC ACT GTG AAG GGC CGA TTC ACC ATC TCC AGA GAC AAT GCC AAG AAC       288
Asp Thr Val Lys Gly Arg Phe Thr Ile Ser Arg Asp Asn Ala Lys Asn
                230                 235                 240

ACC CTG TAC CTG CAA ATG AGC AGT CTG AAG TCT GAG GAC ACA GCC TTG       336
Thr Leu Tyr Leu Gln Met Ser Ser Leu Lys Ser Glu Asp Thr Ala Leu
        245                 250                 255

TAT TAC TGT GCA AGA CAT CGG GGG AGG GAC AGC TCG GGC TAC GTA GGG       384
Tyr Tyr Cys Ala Arg His Arg Gly Arg Asp Ser Ser Gly Tyr Val Gly
260                 265                 270                 275

TAT GCT ATA GAC TAC TGG GGT CAA GGA ACC TCA GTC ACC GTC TCC TCA       432
Tyr Ala Ile Asp Tyr Trp Gly Gln Gly Thr Ser Val Thr Val Ser Ser
                280                 285                 290

GCC AAA ACG ACA CCC CCA TCT GTC TAT CCA TTC CCG GGT TCC               474
Ala Lys Thr Thr Pro Pro Ser Val Tyr Pro Phe Pro Gly Ser
        295                 300                 305
```

(2) INFORMATION FOR SEQ ID NO: 6:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asp Phe Gly Leu Ser Leu Ile Phe Leu Val Leu Val Phe Lys Gly
  1               5                  10                  15
```

-continued

```
Val Leu Cys Asp Val Lys Leu Val Glu Ser Gly Gly Gly Leu Val Lys
            20                  25                  30

Leu Gly Gly Ser Leu Lys Leu Ser Cys Ala Ala Ser Gly Phe Thr Phe
        35                  40                  45

Ser Asn Tyr Tyr Met Ser Trp Val Arg Gln Thr Pro Glu Lys Arg Leu
    50                  55                  60

Glu Phe Val Ala Ala Ile Asn Ser Asn Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Leu
            100                 105                 110

Tyr Tyr Cys Ala Arg His Arg Gly Arg Asp Ser Ser Gly Tyr Val Gly
            115                 120                 125

Tyr Ala Ile Asp Tyr Trp Gly Gln Gly Thr Ser Val Thr Val Ser Ser
130                 135                 140

Ala Lys Thr Thr Pro Pro Ser Val Tyr Pro Phe Pro Gly Ser
145                 150                 155
```

(2) INFORMATION FOR SEQ ID NO: 7:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: monoclonal anti-idiotypic anti-EGFR antibody
        (C) INDIVIDUAL ISOLATE: 5A6 light chain (ix) FEATURE:
        (A) NAME/KEY: CDS
        (B) LOCATION:1..429

(xi) SEQUENCE DESCRIPTION: SEQ ID NO: 7:

```
ATG GTG TCC ACA GCT CAG TTC CTT GTA TTT TTG CTT TTC TGG ATT CCA        48
Met Val Ser Thr Ala Gln Phe Leu Val Phe Leu Leu Phe Trp Ile Pro
160                 165                 170

GCC TCC AGA GGT GAC ATC TTG CTG ACT CAG TCT CCA GCC ATC CTG TCT        96
Ala Ser Arg Gly Asp Ile Leu Leu Thr Gln Ser Pro Ala Ile Leu Ser
175                 180                 185                 190

GTG AGT CCA GGA GAA AGA GTC AGT TTC TCC TGC AGG GCC AGT CAG AGC       144
Val Ser Pro Gly Glu Arg Val Ser Phe Ser Cys Arg Ala Ser Gln Ser
                195                 200                 205

ATT GGC ACA AGC ATA CAC TGG TAT CAA CAA AGA ACA AAT GGT TCT CCA       192
Ile Gly Thr Ser Ile His Trp Tyr Gln Gln Arg Thr Asn Gly Ser Pro
            210                 215                 220

AGG CTT CTC ATA AGT ATA CTT CTG AGT CTA TCT CTG GGA GTC CCT TCC       240
Arg Leu Leu Ile Ser Ile Leu Leu Ser Leu Ser Leu Gly Val Pro Ser
            225                 230                 235

AGG TTT AGT GGC AGT GGA TCA GGG ACA GAT TTT ACT CTT AGC ATC AAC       288
Arg Phe Ser Gly Ser Gly Ser Gly Thr Asp Phe Thr Leu Ser Ile Asn
        240                 245                 250

AGT GTG GAG TCT GAA GAT ATT GCA GAT TAT TAC TGT CAA CAA AGT AAT       336
Ser Val Glu Ser Glu Asp Ile Ala Asp Tyr Tyr Cys Gln Gln Ser Asn
```

```
                    255                 260                 265                 270
AGC TGG CCA TAC ACG TTC GGA GGG GGG ACC AAG TTG GAA ATA AAA CGG              384
Ser Trp Pro Tyr Thr Phe Gly Gly Gly Thr Lys Leu Glu Ile Lys Arg
                        275                 280                 285

GCT GAT GCT GCA CCA ACT GTA TCC ATC TTC CCA CCA TCC ACC CGG                  429
Ala Asp Ala Ala Pro Thr Val Ser Ile Phe Pro Pro Ser Thr Arg
            290                 295                 300
```

(2) INFORMATION FOR SEQ ID NO: 8:

(i) SEQUENCE CHARACTERISTICS:
        (A) LENGTH: 143 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Val Ser Thr Ala Gln Phe Leu Val Phe Leu Leu Phe Trp Ile Pro
  1               5                  10                  15

Ala Ser Arg Gly Asp Ile Leu Leu Thr Gln Ser Pro Ala Ile Leu Ser
                 20                  25                  30

Val Ser Pro Gly Glu Arg Val Ser Phe Ser Cys Arg Ala Ser Gln Ser
             35                  40                  45

Ile Gly Thr Ser Ile His Trp Tyr Gln Gln Arg Thr Asn Gly Ser Pro
         50                  55                  60

Arg Leu Leu Ile Ser Ile Leu Leu Ser Leu Ser Leu Gly Val Pro Ser
 65                  70                  75                  80

Arg Phe Ser Gly Ser Gly Ser Gly Thr Asp Phe Thr Leu Ser Ile Asn
                 85                  90                  95

Ser Val Glu Ser Glu Asp Ile Ala Asp Tyr Tyr Cys Gln Gln Ser Asn
            100                 105                 110

Ser Trp Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Thr Arg
        130                 135                 140
```

(2) INFORMATION FOR SEQ ID NO: 9:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: monoclonal anti-idiotypic anti-EGFR antibody
        (C) INDIVIDUAL ISOLATE: 3B6 heavy chain (ix) FEATURE:
        (A) NAME/KEY: CDS
        (B) LOCATION:1..474

(xi) SEQUENCE DESCRIPTION: SEQ ID NO: 9:

```
ATG GAC TCC AGG CTC AAT TTA GTT TTC CTT GTC CTT GTT TTA AAA GGT               48
Met Asp Ser Arg Leu Asn Leu Val Phe Leu Val Leu Val Leu Lys Gly
145                 150                 155
```

```
GTC CTG TGT GAC GTG AAG CTC GTG GAG TCT GGG GGA GGC TTA GTG AAG        96
Val Leu Cys Asp Val Lys Leu Val Glu Ser Gly Gly Gly Leu Val Lys
160                 165                 170                 175

CTT GGA GGG TCC CTG AAA CTC TCC TGT GCA GCC TCT GGA TTC ACT TTC       144
Leu Gly Gly Ser Leu Lys Leu Ser Cys Ala Ala Ser Gly Phe Thr Phe
                180                 185                 190

AGT AAC TAT TAC ATG TCT TGG GTT CGC CAG ACT CCA GAG AAG AGG CTG       192
Ser Asn Tyr Tyr Met Ser Trp Val Arg Gln Thr Pro Glu Lys Arg Leu
            195                 200                 205

GAG TTT GTC GCA GCC ATT AAT AGT AAT GGT GGT AGC ACC TAC TAT CCA       240
Glu Phe Val Ala Ala Ile Asn Ser Asn Gly Gly Ser Thr Tyr Tyr Pro
        210                 215                 220

GAC ACT GTG AAG GGC CGA TTC ACC ATC TCC AGA GAC AAT GCC AAG AAC       288
Asp Thr Val Lys Gly Arg Phe Thr Ile Ser Arg Asp Asn Ala Lys Asn
    225                 230                 235

ACC CTG TAC CTG CAA ATG AGC AGT CTG AAG TCT GAG GAC ACA GCC TTG       336
Thr Leu Tyr Leu Gln Met Ser Ser Leu Lys Ser Glu Asp Thr Ala Leu
240                 245                 250                 255

TAT TAC TGT GCA AGA CAT CGG GGG AGG GAC AGC TCG GGC TAC GTA GGG       384
Tyr Tyr Cys Ala Arg His Arg Gly Arg Asp Ser Ser Gly Tyr Val Gly
                260                 265                 270

TAT GCT ATA GAC TAC TGG GGT CAA GGA ACC TCA GTC ACC GTC TCC TCA       432
Tyr Ala Ile Asp Tyr Trp Gly Gln Gly Thr Ser Val Thr Val Ser Ser
            275                 280                 285

GCC AAA ACG ACA CCC CCA TCT GTC TAT CCA TTC CCG GGT TCC               474
Ala Lys Thr Thr Pro Pro Ser Val Tyr Pro Phe Pro Gly Ser
        290                 295                 300
```

(2) INFORMATION FOR SEQ ID NO: 10:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Asp Ser Arg Leu Asn Leu Val Phe Leu Val Leu Leu Lys Gly
1               5                   10                  15

Val Leu Cys Asp Val Lys Leu Val Glu Ser Gly Gly Gly Leu Val Lys
            20                  25                  30

Leu Gly Gly Ser Leu Lys Leu Ser Cys Ala Ala Ser Gly Phe Thr Phe
        35                  40                  45

Ser Asn Tyr Tyr Met Ser Trp Val Arg Gln Thr Pro Glu Lys Arg Leu
    50                  55                  60

Glu Phe Val Ala Ala Ile Asn Ser Asn Gly Gly Ser Thr Tyr Tyr Pro
65                  70                  75                  80

Asp Thr Val Lys Gly Arg Phe Thr Ile Ser Arg Asp Asn Ala Lys Asn
            85                  90                  95

Thr Leu Tyr Leu Gln Met Ser Ser Leu Lys Ser Glu Asp Thr Ala Leu
        100                 105                 110

Tyr Tyr Cys Ala Arg His Arg Gly Arg Asp Ser Ser Gly Tyr Val Gly
    115                 120                 125

Tyr Ala Ile Asp Tyr Trp Gly Gln Gly Thr Ser Val Thr Val Ser Ser
130                 135                 140

Ala Lys Thr Thr Pro Pro Ser Val Tyr Pro Phe Pro Gly Ser
145                 150                 155
```

(2) INFORMATION FOR SEQ ID NO: 11:

(i) SEQUENCE CHARACTERISTICS:
    (A) LENGTH: 438 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
    (A) ORGANISM: monoclonal anti-idiotypic anti-EGFR antibody
    (C) INDIVIDUAL ISOLATE: 3B6 light chain (ix) FEATURE:
    (A) NAME/KEY: CDS
    (B) LOCATION:1..438

(xi) SEQUENCE DESCRIPTION: SEQ ID NO: 11:

```
ATG GAG TCA GAC ACA CTC CTG CTA TGG GTA CTG CTG CTC TGG GTT CCA        48
Met Glu Ser Asp Thr Leu Leu Leu Trp Val Leu Leu Leu Trp Val Pro
160             165                 170

GGT TCC ACT GGT GAC ATT GTG CTG ACA CAG TCT CCT GCT TCC TTA GCT        96
Gly Ser Thr Gly Asp Ile Val Leu Thr Gln Ser Pro Ala Ser Leu Ala
175             180                 185                 190

GTA TCT CTG GGG CAG AGG GCC ACC ATC TCA TAC AGG GCC AGC AAA AGT       144
Val Ser Leu Gly Gln Arg Ala Thr Ile Ser Tyr Arg Ala Ser Lys Ser
                195                 200                 205

GTC AGT ACA TCT GGC TAT AGT TAT ATG CAC TGG AAC CAA CAG AAA CCA       192
Val Ser Thr Ser Gly Tyr Ser Tyr Met His Trp Asn Gln Gln Lys Pro
                210                 215                 220

GGA CAG CCA CCC AGA CTC CTC ATC TAT CTT GTA TCC AAC CTA GAA TCT       240
Gly Gln Pro Pro Arg Leu Leu Ile Tyr Leu Val Ser Asn Leu Glu Ser
                225                 230                 235

GGG GTC CCT GCC AGG TTC AGT GGC AGT GGG TCT GGG ACA GAT TTC ACC       288
Gly Val Pro Ala Arg Phe Ser Gly Ser Gly Ser Gly Thr Asp Phe Thr
                240                 245                 250

CTC AAC ATC CAT CCT GTG GAG GAG GAG GAT GCC TCA ACC TAT TAC TGT       336
Leu Asn Ile His Pro Val Glu Glu Glu Asp Ala Ser Thr Tyr Tyr Cys
255                 260                 265                 270

CAG CAC ATT AGG GAG GTC TAC ACG TTC GGA GGG GGG ACC AAG CTG GAA       384
Gln His Ile Arg Glu Val Tyr Thr Phe Gly Gly Gly Thr Lys Leu Glu
                275                 280                 285

ATA AAA CGG GCT GAT GCT GCA CCA ACT GTA TCC ATC TTC CCA CCA TCC       432
Ile Lys Arg Ala Asp Ala Ala Pro Thr Val Ser Ile Phe Pro Pro Ser
                290                 295                 300

ACC CGG                                                                438
Thr Arg
```

(2) INFORMATION FOR SEQ ID NO: 12:

(i) SEQUENCE CHARACTERISTICS:
    (A) LENGTH: 146 amino acids
    (B) TYPE: amino acid
    (D) TOPOLOGY: linear (ii) MOLECULE TYPE: protein (xi) SEQUENCE DESCRIPTION: SEQ ID NO: 12:

```
Met Glu Ser Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
```

```
                      20                   25                    30
Val Ser Leu Gly Gln Arg Ala Thr Ile Ser Tyr Arg Ala Ser Lys Ser
             35                  40                  45
Val Ser Thr Ser Gly Tyr Ser Tyr Met His Trp Asn Gln Gln Lys Pro
         50                  55                  60
Gly Gln Pro Pro Arg Leu Leu Ile Tyr Leu Val Ser Asn Leu Glu Ser
 65                  70                  75                  80
Gly Val Pro Ala Arg Phe Ser Gly Ser Gly Ser Gly Thr Asp Phe Thr
                 85                  90                  95
Leu Asn Ile His Pro Val Glu Glu Glu Asp Ala Ser Thr Tyr Tyr Cys
            100                 105                 110
Gln His Ile Arg Glu Val Tyr Thr Phe Gly Gly Gly Thr Lys Leu Glu
            115                 120                 125
Ile Lys Arg Ala Asp Ala Ala Pro Thr Val Ser Ile Phe Pro Pro Ser
        130                 135                 140
Thr Arg
145

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:13:

Gly Tyr Val Gly Tyr Ala Ile Asp Tyr
1               5
```